US011517363B2

(12) United States Patent
Nayet et al.

(10) Patent No.: US 11,517,363 B2
(45) Date of Patent: Dec. 6, 2022

(54) SCREW DRIVER AND COMPLIMENTARY SCREWS

(71) Applicant: Warsaw Orthopedic, Inc., Warsaw, IN (US)

(72) Inventors: Jerome Nayet, St. Genis-Pouilly (FR); Loic Josse, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/123,906

(22) Filed: Dec. 16, 2020

(65) Prior Publication Data
US 2022/0133379 A1    May 5, 2022

(30) Foreign Application Priority Data

Nov. 5, 2020  (WO) .................. PCT/IB2020/000932
Nov. 5, 2020  (WO) .................. PCT/IB2020/000942
Nov. 5, 2020  (WO) .................. PCT/IB2020/000953

(51) Int. Cl.
*A61B 17/88*     (2006.01)
*A61F 2/46*      (2006.01)
(Continued)

(52) U.S. Cl.
CPC ...... *A61B 17/8886* (2013.01); *A61F 2/30771* (2013.01); *A61F 2/447* (2013.01);
(Continued)

(58) Field of Classification Search
CPC .............. A61B 17/8875; A61B 17/888; A61B 17/8891; A61B 17/862; A61B 17/8886;
(Continued)

(56) References Cited

U.S. PATENT DOCUMENTS 1,677,337 A    7/1928   Grove
3,847,154 A   11/1974   Nordin
(Continued)

FOREIGN PATENT DOCUMENTS

CN    107 137 166 A     9/2017
EP       2954860 A2    12/2015
(Continued)

OTHER PUBLICATIONS

International Search Report and Written Opinion, PCT/IB2020/000932, dated Jul. 29, 2021.
(Continued)

*Primary Examiner* — Samuel S Hanna
(74) *Attorney, Agent, or Firm* — Fox Rothschild LLP; Paul Marshall Ticer

(57) ABSTRACT

Disclosed screwdrivers may include a rotatable drive shaft having a drive portion disposed at a distal end thereof, and a drive end disposed at a proximal end thereof. Disclosed screwdrivers may include an angled tip portion that is angled with respect to the longitudinal direction, and a mechanism configured to transfer a rotational force applied to the drive portion of the drive shaft through the angled tip portion to the drive end of the drive shaft. Disclosed screwdrivers may include an elastic retaining clip configured to have a bone screw securely attached therein at a clipping force and progressively release the bone screw therein at an extraction force. Disclosed screwdrivers may include at least one spring contacting the elastic retaining clip and the angled tip portion that is configured to facilitate the progressive release of the bone screw.

16 Claims, 23 Drawing Sheets

(51) Int. Cl.
*A61F 2/30* (2006.01)
*A61F 2/44* (2006.01)

(52) U.S. Cl.
CPC ..... *A61F 2/4611* (2013.01); *A61F 2002/3093* (2013.01); *A61F 2002/30405* (2013.01); *A61F 2002/30518* (2013.01); *A61F 2002/30538* (2013.01); *A61F 2002/30579* (2013.01); *A61F 2002/30774* (2013.01); *A61F 2002/30841* (2013.01); *A61F 2002/30935* (2013.01)

(58) Field of Classification Search
CPC .............. A61B 17/162; A61B 17/1622; A61B 17/1633; A61B 17/1671; A61B 2090/08021; A61B 17/1617; A61B 17/1624; A61B 17/1862; A61B 2017/0046; A61F 2/4611; A61F 2/30771; A61F 2/447; A61F 2/4603; A61F 2002/30405; A61F 2002/30518; A61F 2002/30579; A61F 2002/30774; A61F 2002/30841; A61F 2002/30935; A61F 2002/4627

See application file for complete search history.

(56) References Cited

U.S. PATENT DOCUMENTS

| | | |
|---|---|---|
| 4,716,894 A | 1/1988 | Lazzeri et al. |
| 5,228,811 A | 7/1993 | Potter |
| 5,284,483 A | 2/1994 | Johnson et al. |
| 5,653,763 A | 8/1997 | Errico et al. |
| 5,797,918 A | 8/1998 | McGuire et al. |
| 5,941,885 A | 8/1999 | Jackson |
| 5,971,987 A | 10/1999 | Huxel et al. |
| 6,524,238 B2 | 2/2003 | Velikaris et al. |
| 7,188,626 B2 | 3/2007 | Foley et al. |
| 7,255,700 B2 | 8/2007 | Kaiser et al. |
| 7,316,532 B2 | 1/2008 | Matthys-Mark |
| 7,637,909 B2 | 12/2009 | Lechot et al. |
| 7,824,428 B2 | 11/2010 | Mikkonen et al. |
| 8,328,872 B2 | 12/2012 | Duffield et al. |
| 8,419,797 B2 | 4/2013 | Biedermann et al. |
| 8,608,785 B2 | 12/2013 | Reed et al. |
| 8,668,419 B2 | 3/2014 | Hardt et al. |
| 8,740,983 B1 | 6/2014 | Arnold et al. |
| 8,753,396 B1 | 6/2014 | Hockett et al. |
| 8,840,668 B1 | 9/2014 | Donahoe et al. |
| 8,852,252 B2 | 10/2014 | Venturini et al. |
| 8,882,813 B2 | 11/2014 | Jones et al. |
| 9,005,292 B2 | 4/2015 | Melamed |
| 9,017,412 B2 | 4/2015 | Wolters et al. |
| 9,138,331 B2 | 9/2015 | Aferzon |
| 9,161,841 B2 | 10/2015 | Kana et al. |
| 9,179,952 B2 | 11/2015 | Biedermann et al. |
| 9,192,483 B1 | 11/2015 | Radcliffe et al. |
| 9,486,327 B2 | 11/2016 | Martynova et al. |
| 9,517,098 B2 | 12/2016 | Anderson |
| 9,526,620 B2 | 12/2016 | Slivka et al. |
| 9,539,103 B2 | 1/2017 | McLaughlin et al. |
| 9,545,320 B2 | 1/2017 | Padovani et al. |
| 9,566,166 B2 | 2/2017 | Parry et al. |
| 9,572,681 B2 | 2/2017 | Mathieu et al. |
| 9,579,213 B2 | 2/2017 | Bal et al. |
| 9,585,766 B2 | 3/2017 | Robinson |
| 9,585,767 B2 | 3/2017 | Robinson |
| 9,592,129 B2 | 3/2017 | Slivka et al. |
| 9,603,643 B2 | 3/2017 | Reed et al. |
| 9,615,936 B2 | 4/2017 | Duffield et al. |
| 9,649,198 B2 | 5/2017 | Wolters et al. |
| 9,675,465 B2 | 6/2017 | Padovani et al. |
| 9,693,871 B2 | 7/2017 | Richerme et al. |
| 9,763,722 B2 | 9/2017 | Roybal |
| 9,808,352 B2 | 11/2017 | Suddaby et al. |
| 9,833,333 B2 | 12/2017 | Duffield et al. |
| 9,833,336 B2 | 12/2017 | Davenport et al. |
| 9,848,996 B2 | 12/2017 | Faulhaber |
| 9,867,715 B2 | 1/2018 | McLaughlin et al. |
| 9,925,064 B2 | 3/2018 | Duffield et al. |
| 9,949,775 B2 | 4/2018 | Reed et al. |
| 9,962,202 B2 | 5/2018 | Anderson |
| 9,968,461 B2 | 5/2018 | Zappacosta et al. |
| 9,980,826 B2 | 5/2018 | Martynova et al. |
| 9,987,141 B2 | 6/2018 | Duffield et al. |
| 10,028,842 B2 | 7/2018 | Gray et al. |
| 10,034,771 B2 | 7/2018 | Capote et al. |
| 10,034,773 B2 | 7/2018 | McLaughlin et al. |
| 10,058,431 B2 | 8/2018 | Tyber et al. |
| 10,080,669 B2 | 9/2018 | Davenport et al. |
| 10,111,758 B2 | 10/2018 | Robinson |
| 10,137,002 B2 | 11/2018 | Padovani et al. |
| 10,154,914 B2 | 12/2018 | Robinson |
| 10,159,584 B2 | 12/2018 | Carnes et al. |
| 10,179,053 B2 | 1/2019 | Zappacosta et al. |
| 10,251,643 B2 | 4/2019 | Moskowitz et al. |
| 10,314,622 B2 | 6/2019 | Brumfield et al. |
| 10,327,909 B2 | 6/2019 | Baynham |
| 10,390,964 B2 | 8/2019 | Faulhaber |
| 10,456,122 B2 | 10/2019 | Koltz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,537,438 B2 | 1/2020 | Martynova et al. |
| 10,575,889 B2 | 3/2020 | Roybal |
| 10,575,960 B2 | 3/2020 | Duffield et al. |
| 10,582,959 B2 | 3/2020 | Langer et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,653,458 B2 | 5/2020 | Tanaka et al. |
| 10,675,157 B2 | 6/2020 | Zakelj et al. |
| 10,702,393 B2 | 7/2020 | Davenport et al. |
| 10,709,575 B2 | 7/2020 | Robinson |
| 10,772,737 B2 | 9/2020 | Gray et al. |
| 10,786,364 B2 | 9/2020 | Davenport et al. |
| 10,786,369 B2 | 9/2020 | Carnes et al. |
| 10,874,447 B2 | 12/2020 | Tanaka et al. |
| 10,874,522 B2 | 12/2020 | Weiman |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |

(56) References Cited

U.S. PATENT DOCUMENTS

| | | |
|---|---|---|
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 2002/0183762 A1 | 12/2002 | Anderson et al. |
| 2005/0228398 A1 | 10/2005 | Rathbun et al. |
| 2006/0260446 A1 | 11/2006 | Chang |
| 2007/0218750 A1 | 9/2007 | Corrao et al. |
| 2007/0233150 A1 | 10/2007 | Blain et al. |
| 2007/0270859 A1 | 11/2007 | Companioni et al. |
| 2008/0058804 A1 | 3/2008 | Lechot et al. |
| 2008/0132959 A1 | 6/2008 | Mikkonen et al. |
| 2008/0140207 A1 | 6/2008 | Olmos et al. |
| 2010/0076440 A1 | 3/2010 | Pamichev et al. |
| 2010/0152853 A1 | 6/2010 | Kirschman |
| 2010/0286777 A1 | 11/2010 | Errico et al. |
| 2011/0118843 A1 | 5/2011 | Mathieu et al. |
| 2011/0153020 A1 | 6/2011 | Abdelgany et al. |
| 2011/0218572 A1 | 9/2011 | Lechmann et al. |
| 2012/0004732 A1 | 1/2012 | Goel et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0143195 A1 | 6/2012 | Sander |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215313 A1 | 8/2012 | Saidha et al. |
| 2013/0184823 A1 | 7/2013 | Malberg |
| 2013/0211526 A1 | 8/2013 | Alheidt et al. |
| 2013/0226191 A1 | 8/2013 | Thoren et al. |
| 2013/0304136 A1 | 11/2013 | Gourlaouen-Preissler et al. |
| 2014/0018816 A1 | 1/2014 | Fenn et al. |
| 2014/0114321 A1 | 4/2014 | Davenport et al. |
| 2014/0114420 A1 | 4/2014 | Robinson |
| 2014/0148904 A1 | 5/2014 | Robinson |
| 2014/0249631 A1 | 9/2014 | Weiman |
| 2014/0303674 A1 | 10/2014 | Sasing |
| 2014/0364855 A1* | 12/2014 | Stoll ................. A61B 17/1615 606/80 |
| 2015/0238236 A1 | 8/2015 | Sasing |
| 2015/0354635 A1 | 12/2015 | McClymont et al. |
| 2016/0022434 A1 | 1/2016 | Robinson |
| 2016/0095710 A1 | 4/2016 | Juszczyk et al. |
| 2016/0095718 A1 | 4/2016 | Burkhardt et al. |
| 2016/0199073 A1 | 7/2016 | Nino et al. |
| 2016/0242930 A1 | 8/2016 | Duffield et al. |
| 2016/0278830 A1 | 9/2016 | Arrington |
| 2016/0367377 A1 | 12/2016 | Faulhaber |
| 2017/0112630 A1 | 4/2017 | Kuyler et al. |
| 2017/0156882 A1 | 6/2017 | Rathbun et al. |
| 2017/0156884 A1 | 6/2017 | Rathbun et al. |
| 2017/0189204 A1* | 7/2017 | Riemhofer ......... A61B 17/8877 |
| 2017/0202678 A1 | 7/2017 | Duffield et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0246006 A1 | 8/2017 | Carnes et al. |
| 2017/0367842 A1 | 12/2017 | Predick et al. |
| 2018/0000606 A1 | 1/2018 | Hessler et al. |
| 2018/0036136 A1 | 2/2018 | Duffield et al. |
| 2018/0104066 A1 | 4/2018 | Bae et al. |
| 2018/0193160 A1 | 7/2018 | Hsu et al. |
| 2018/0256362 A1 | 9/2018 | Slivka et al. |
| 2018/0280142 A1 | 10/2018 | Schultz et al. |
| 2018/0325574 A1 | 11/2018 | Bjork et al. |
| 2018/0338841 A1 | 11/2018 | Miller et al. |
| 2019/0046329 A1 | 2/2019 | Padovani et al. |
| 2019/0105175 A1 | 4/2019 | Zappacosta et al. |
| 2019/0133779 A1 | 5/2019 | McLaughlin et al. |
| 2019/0247098 A1 | 8/2019 | Brumfield et al. |
| 2019/0262009 A1 | 8/2019 | Cheng |
| 2019/0298416 A1 | 10/2019 | Rezach |
| 2019/0298524 A1 | 10/2019 | Lauf et al. |
| 2019/0328539 A1 | 10/2019 | Suh et al. |
| 2019/0329388 A1 | 10/2019 | Erickson et al. |
| 2019/0336304 A1 | 11/2019 | Burkhardt et al. |
| 2019/0358049 A1 | 11/2019 | Faulhaber |
| 2019/0380840 A1 | 12/2019 | Tyber et al. |
| 2020/0060844 A1 | 2/2020 | Mathieu et al. |
| 2020/0069316 A1 | 3/2020 | DeSoutter et al. |
| 2020/0093526 A1 | 3/2020 | Daly et al. |
| 2020/0093607 A1 | 3/2020 | Davenport et al. |
| 2020/0138593 A1 | 5/2020 | Martynova et al. |
| 2020/0179120 A1 | 6/2020 | Bielenstein et al. |
| 2020/0205993 A1 | 7/2020 | Davenport et al. |
| 2020/0214754 A1 | 7/2020 | Bowen et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0281741 A1 | 9/2020 | Grotz |
| 2020/0405497 A1 | 12/2020 | Olmos et al. |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Weiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |

(56) References Cited

U.S. PATENT DOCUMENTS

| | | |
|---|---|---|
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2022/0015924 A1 | 1/2022 | Freedman et al. |
| 2022/0047312 A1 | 2/2022 | Seykora et al. |
| 2022/0133336 A1 | 5/2022 | Tsai et al. |

FOREIGN PATENT DOCUMENTS

| | | |
|---|---|---|
| EP | 3031424 A1 | 6/2016 |
| EP | 3 069 694 A1 | 9/2016 |
| EP | 3213720 A1 | 9/2017 |
| FR | 2781998 A1 | 2/2000 |
| FR | 3082115 A1 | 12/2019 |
| KR | 102192022 B1 | 12/2020 |
| WO | 2006116850 A1 | 11/2006 |
| WO | 2012139022 A2 | 10/2012 |
| WO | 2015063721 A1 | 5/2015 |
| WO | 2015198335 A1 | 12/2015 |
| WO | 2016057940 A1 | 4/2016 |
| WO | 2018049227 A1 | 3/2018 |
| WO | 2021055323 A1 | 3/2021 |

OTHER PUBLICATIONS

International Search Report and Written Opinion, PCT/IB2020/000942, dated Aug. 10, 2021.
International Search Report, and Written Opinion for Application. No. PCT/US2019/019067, dated Jun. 3, 2019.
International Search Report and Written Opinion for Application No. PCT/US2019/019060, dated Jun. 5, 2019.
International Search Report and Written Opinion in Application No. PCT/US2022/016809 dated Jul. 27, 2022.
International Search Report and Written Opinion in Application No. PCT/US2022/027695 dated Jul. 27, 2022.
International Search Report and Written Opinion in Application No. PCT/US2022/027200 dated Aug. 19, 2022.
International Search Report and Written Opinion in Application No. PCT/US2022/030094 dated Sep. 16, 2022.

* cited by examiner

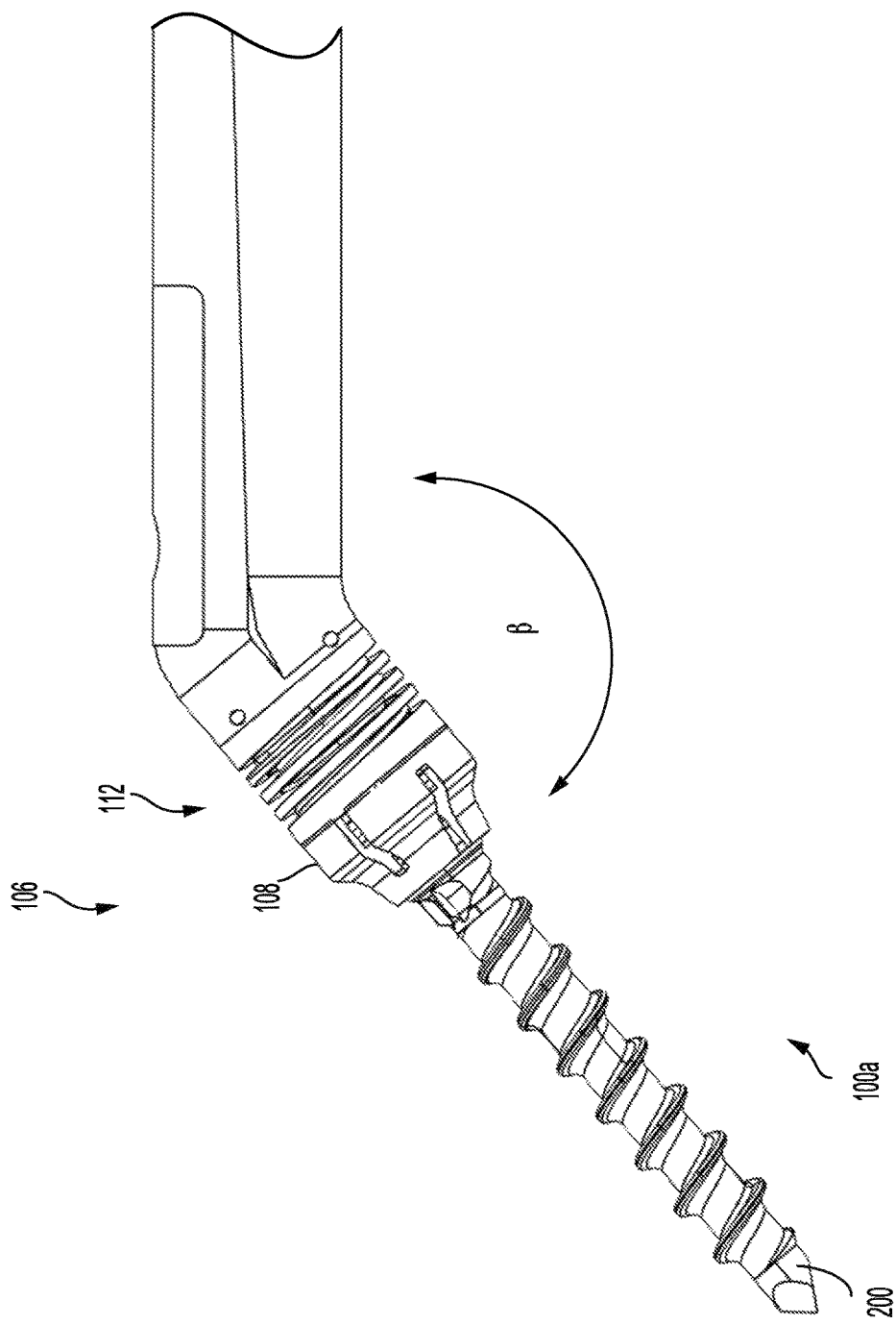

SCREW DRIVER AND COMPLIMENTARY SCREWS

CROSS-REFERENCE TO RELATED APPLICATIONS

This application hereby claims priority to and incorporates by reference co-related patent applications, PCT/FR2020/000257, titled Expandable Inter-Body Device, System, and Method, filed Nov. 5, 2020; PCT/FR2020/000259, titled Screwdriver and Complimentary Screws, filed Nov. 5, 2020; and PCT/FR2020/000258, titled Expandable Inter-Body Device, System, and Method, filed Nov. 5, 2020. The contents of each are hereby incorporated in their entireties.

FIELD

The present technology is generally related to screwdrivers for installing, removing, and/or manipulating complimentary bone screws.

BACKGROUND

The installation and insertion of bone screws in a patient poses many risks. Some of these risks may include the loss of a bone screw in the patient, which can have dramatic consequences and even lead to death in some cases. Additionally, conventional screwdrivers and related tools are often unsuitable for avoiding anatomical features, such as the pelvic ring, rib cage, iliac crest, etc., for example. Additionally, conventional screwdrivers are not be well suited for installation of bone screws in angled bone plates and/or angled apertures of spinal implants, for example. There is a need for screwdrivers that can securely connect to a complimentary bone screw with sufficient force that the bone screw will not become accidentally detached during the initial positioning and installation of the bone screw. Additionally, there is a need for screwdrivers that are optimized for the installation of bone screws to secure spinal implants to adjacent vertebrae of a patient according to various surgical techniques including anterior techniques, lateral techniques, and oblique techniques.

SUMMARY

In one aspect, the present disclosure provides for a screwdriver, including: a rotatable drive shaft, the drive shaft including a drive portion disposed at a distal end thereof, a drive end disposed at a proximal end thereof, and a main shaft portion extending in a longitudinal direction through a housing; an angled tip portion disposed at the proximal end, the angled tip portion being angled with respect to the longitudinal direction, the drive end of the drive shaft extending through the angled tip portion; and a mechanism configured to transfer a rotational force applied to the drive portion of the drive shaft through the angled tip portion to the drive end of the drive shaft. The screwdriver may further include: an elastic retaining clip configured to have a bone screw securely attached therein at a clipping force and progressively release the bone screw therein at an extraction force, the elastic retaining clip being removably and operably coupled with the drive end of the drive shaft; and a first spring contacting the elastic retaining clip and the angled tip portion, the first spring being configured to facilitate the progressive release of the bone screw.

In another aspect, the present disclosure provides a positioning handle can be configured for an end user to securely maintain the screwdriver in place.

In another aspect, the present disclosure provides that the positioning handle may be angled away from the housing and extends towards the distal end.

In another aspect, the present disclosure provides that the elastic retaining clip can be configured to rotate with the drive portion of the drive shaft.

In another aspect, the present disclosure provides that the screwdriver further may include a second spring configured to facilitate the progressive release of the bone screw, that the first spring and second spring each contact the elastic retaining clip and the angled tip portion, and that the first spring is disposed, at least partly, within a central cavity of the second spring.

In another aspect, the present disclosure provides that the elastic retaining clip may further include at least one bump configured to facilitate the retention of the bone screw by contacting the bone screw.

In another aspect, the present disclosure provides that the bone screw may include an indent extending circumferentially around a head portion of the bone screw and the at least one bump is configured to contact the bone screw and be seated, at least partially, within the indent.

In another aspect, the present disclosure provides that the elastic retaining clip may further comprise at least one protrusion disposed at an end portion thereof configured to facilitate the retention of the bone screw.

In another aspect, the present disclosure provides that the at least one protrusion may be radially inset with respect to a head portion of the bone screw and is configured to contact an end portion of the head portion of the bone screw to thereby facilitate the retention of the bone screw.

In another aspect, the present disclosure provides that the elastic retaining clip may further comprise at least one tapered portion that progressively tapers along the retaining clip to an outermost end thereof.

In another aspect, the present disclosure provides that the tapered portion may be configured to contact a circumferential surface of a head portion of the bone screw.

In another aspect, the present disclosure provides that the mechanism may be a geared mechanism that includes a first group of teeth disposed at a proximal end of the main shaft portion and extending in the longitudinal direction, and a second group of teeth disposed at a distal end of the drive end and extending in a direction parallel with respect to the angled tip portion. Additionally, the first group of teeth are meshed with the second group of teeth to thereby transfer a rotational force applied to the drive portion to the drive end.

In another aspect, the present disclosure provides that the mechanism may be a joint mechanism further including: a spherical portion seated in a housing area of the tip portion, the spherical portion being operably coupled to the main shaft portion at a proximal end thereof and fixedly coupled to the drive end at a distal end thereof, and that the spherical portion includes at least one aperture configured to receive a proximal end of the main shaft portion therein and a pin to operably couple to the main shaft portion.

In another aspect, the present disclosure provides that the mechanism may be a flexible shaft, further including: a straight portion seated in main shaft portion and extending in the longitudinal direction, being operably coupled to the flexible part, and a second straight portion at a distal end of the drive end and extending in a direction parallel with respect to the angled tip portion. Additionally the flexible part can be made of an assembly of springs. Alternatively the flexible shaft with successive and organized cuts making the shaft flexible.

In another aspect, the present disclosure provides that the clipping force may be, for example, about 2.5 N and the extraction force is about 15 N.

In another aspect, the present disclosure provides that a ratio of the clipping force to the extraction force may be, for example, about 1:6.

In another aspect, the present disclosure provides, for example, a manual hand driver configured to operably couple with the drive portion of the drive shaft.

In another aspect, the present disclosure provides, for example, a powered driver configured to operably couple with the drive portion of the drive shaft.

In another aspect, the present disclosure provides a screwdriver system, the system including, for example: a rotatable drive shaft, the drive shaft including a drive portion disposed at a distal end thereof, a drive end disposed at a proximal end thereof, and a main shaft portion extending in a longitudinal direction through a housing, and an angled tip portion disposed at the proximal end, the angled tip portion being angled with respect to the longitudinal direction, the drive end of the drive shaft extending through the angled tip portion. The system may further include a mechanism configured to transfer a rotational force applied to the drive portion of the drive shaft through the angled tip portion to the drive end of the drive shaft and a first elastic retaining clip configured to couple and uncouple from the drive end, the first elastic retaining clip being further configured to securely retain a first bone screw therein at a first clipping force and progressively release the first bone screw therein at a first extraction force. The system may further include: a second elastic retaining clip configured to couple and uncouple from the drive end, the second elastic retaining clip being further configured to securely retain a second bone screw therein at a second clipping force and progressively release the second bone screw therein at a second extraction force, and at least one spring configured to contact either one of the first elastic retaining clip and the second elastic retaining clip at a time and the angled tip portion, the at least one spring being configured to facilitate the progressive release of either one of the first bone screw and second bone screw at a time. Additionally, the first bone screw and the second bone screw may include different circumferential surfaces at a head portion thereof, and the first retaining clip includes at least one first retaining feature corresponding to the circumferential surface of the first bone screw and the second retaining clip includes at least one second retaining feature corresponding to the circumferential surface of the second bone screw.

In another aspect, the present disclosure provides a method for installing a bone screw in an aperture of a medical device or plate, including, for example: selecting at least one bone screw for installation in an anatomical feature of a patient, and providing a screwdriver configured to drive the at least one bone screw. The screwdriver may include: a rotatable drive shaft, the drive shaft including a drive portion disposed at a distal end thereof, a drive end disposed at a proximal end thereof, and a main shaft portion extending in a longitudinal direction through a housing, and an angled tip portion disposed at the proximal end, the angled tip portion being angled with respect to the longitudinal direction, the drive end of the drive shaft extending through the angled tip portion. The screwdriver may further include: a mechanism configured to transfer a rotational force applied to the drive portion of the drive shaft through the angled tip portion to the drive end of the drive shaft, an elastic retaining clip configured to have the at least one selected bone screw securely attached therein at a clipping force and progressively release the at least one selected bone screw therein at an extraction force, the elastic retaining clip being removably and operably coupled with the drive end of the drive shaft, and at least one spring contacting the elastic retaining clip and the angled tip portion, the at least one spring being configured to facilitate the progressive release of the at least one selected bone screw.

In another aspect, the present disclosure provides a method including, for example, clipping the at least one bone screw to the retaining clip by pushing a head portion of the at least one selected bone screw into the retaining clip at a force that exceeds the clipping force, driving the at least one bone screw into the anatomical feature of the patient, and automatically and progressively releasing the at least one bone screw after the at least one bone screw is sufficiently driven into the anatomical feature of the patient such that the pulling force exceeds the extraction force.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 3 is a magnified view of the tip portion of an example screwdriver in accordance with the principles of the present disclosure;

FIG. 23 is a perspective view of an example medical device that includes bone screw apertures that example screwdrivers of the present disclosure may progressively drive a bone screw through.

DETAILED DESCRIPTION

Figure 1:
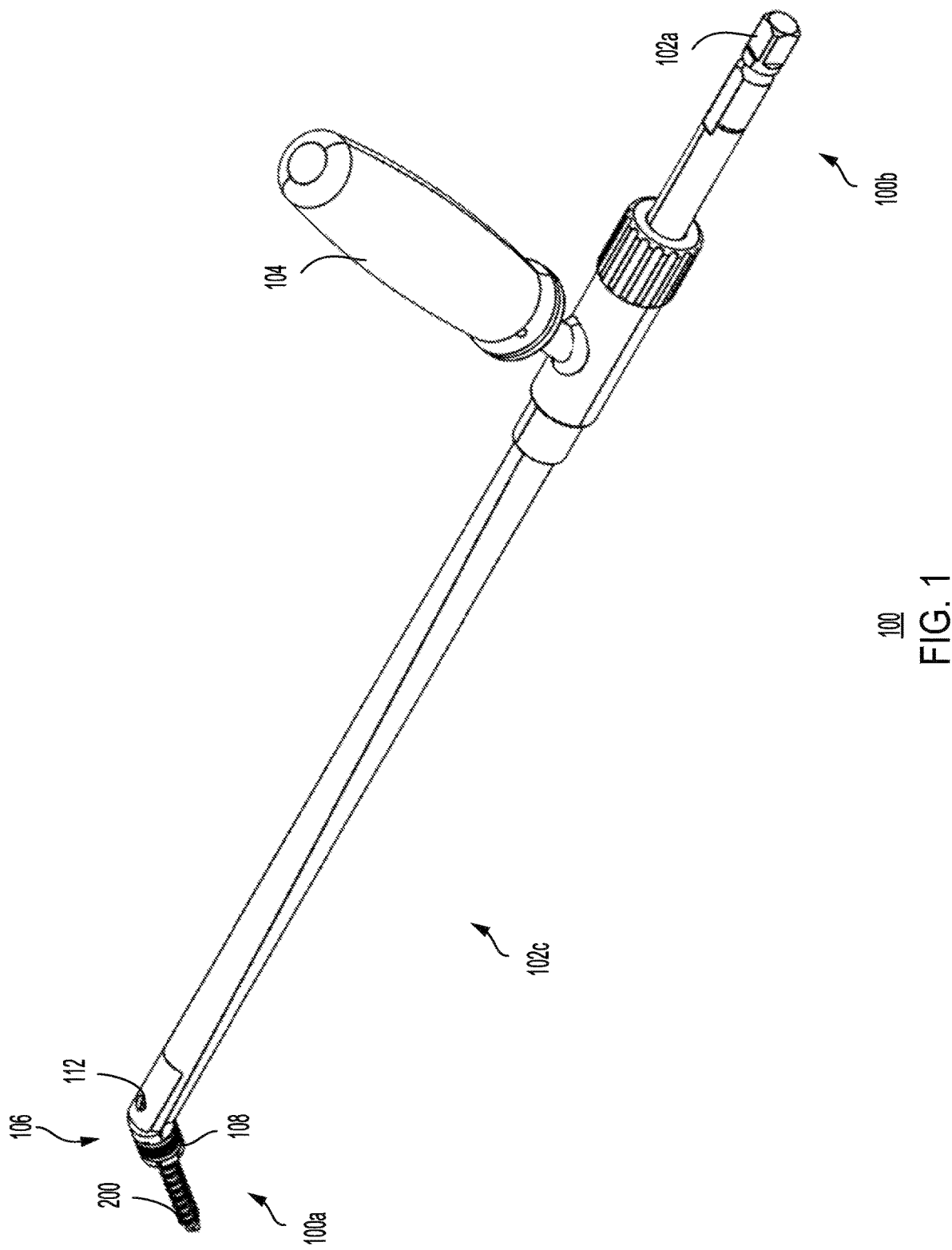
FIG. 1 is a perspective view of an example screwdriver in accordance with the principles of the present disclosure.

As used herein, standard anatomical terms of location have their ordinary meaning as they would be understood by a person of ordinary skill in the art unless clearly defined or explained otherwise. It should be understood that various aspects disclosed herein may be combined in different combinations than the combinations specifically presented in the description and accompanying drawings. For example, characteristics of one embodiment may be combined or substituted with characteristics of another different embodiment unless those characteristics are clearly explained as being mutually exclusive. It should also be understood that, depending on the example, certain acts or events of any of the processes or methods described herein may be performed in a different sequence, may be added, merged, or left out altogether (e.g., all described acts or events may not be necessary to carry out the disclosed techniques and methods). In addition, while certain aspects of this disclosure are described as being performed by a single module, unit, or component for purposes of clarity, it should be understood that the techniques of this disclosure may be performed by a combination of units, modules, or components associated with, for example, a medical device such as a screwdriver.

In some embodiments, the present disclosure is directed to a screwdriver that is optimized for a medical setting and various types of surgical techniques, including anterior surgical techniques, lateral surgical techniques, and oblique surgical techniques. In some embodiments, a screwdriver may be optimized to secure a spinal implant between adjacent vertebrae by securing at least one complimentary bone screw to the spinal implant and into an adjacent vertebrae. In some embodiments, and as mentioned above, the present disclosure may be employed in conjunction with spinal implants to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics.

In some embodiments, the disclosed example screwdrivers may be alternatively employed in a surgical treatment with a patient in a prone or supine position, and/or employ various surgical approaches to the spine, including anterior, posterior, posterior mid-line, direct lateral, postero-lateral oblique, and/or antero lateral oblique approaches, and in other body regions. The present disclosure may also be alternatively employed with procedures for treating the lumbar, cervical, thoracic, sacral and pelvic regions of a spinal column. The screwdriver of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value and all numerical values therebetween. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior." Generally, similar spatial references of different aspects or components, e.g., a "proximal end" of one component and a "proximal end" of a different component, indicate similar spatial orientation and/or positioning, i.e., that each "proximal end" is situated on or directed towards the same end of the device. Further, the use of various spatial terminology herein should not be interpreted to limit the various insertion techniques or orientations of the implant relative to the positions in the spine.

As used in the specification and including the appended claims, "treating" or "treatment" of a disease or condition refers to performing a procedure that may include administering one or more drugs, biologics, bone grafts (including allograft, autograft, xenograft, for example) or bone-growth promoting materials to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of disclosed embodiments described herein can be fabricated from biologically acceptable materials suitable for medical applications, including metals, synthetic polymers, ceramics and bone material and/or their composites. For example, the components of disclosed screwdrivers and bone screws, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaprolactone and their combinations.

Various components of disclosed embodiments may be formed or constructed of material composites, including but not limited to the above-described materials, to achieve various desired characteristics such as strength, rigidity, elasticity, compliance, biomechanical performance, durability and radiolucency or imaging preference. The components of expandable spinal implant system, individually or collectively, may also be fabricated from a heterogeneous material such as a combination of two or more of the above-described materials. The components of disclosed embodiments may be monolithically formed, integrally connected or include fastening elements and/or instruments, as described herein. For example, in some embodiments components comprising PEEK and/or titanium structures with radiolucent markers (such as tantalum pins and/or spikes) selectively placed in a screwdriver or a spinal implant the screwdriver is configured to secure to an adjacent vertebrae to provide a medical practitioner with placement and/or sizing information to assist a surgeon with placement, removal, or manipulation of a corresponding bone screw. The components of disclosed embodiments may be formed using a variety of subtractive and additive manufacturing techniques, including, but not limited to machining, milling, extruding, molding, 3D-printing, sintering, coating, vapor deposition, and laser/beam melting. Furthermore, various components of the expandable spinal implant system may be coated or treated with a variety of additives or coatings to improve biocompatibility, bone growth promotion or other features. For example, disclosed bone screws, may be selectively coated with bone growth promoting or bone ongrowth promoting surface treatments that may include, but are not limited to: titanium coatings (solid, porous or textured), hydroxyapatite coatings, or titanium plates (solid, porous or textured).

Figure 2:
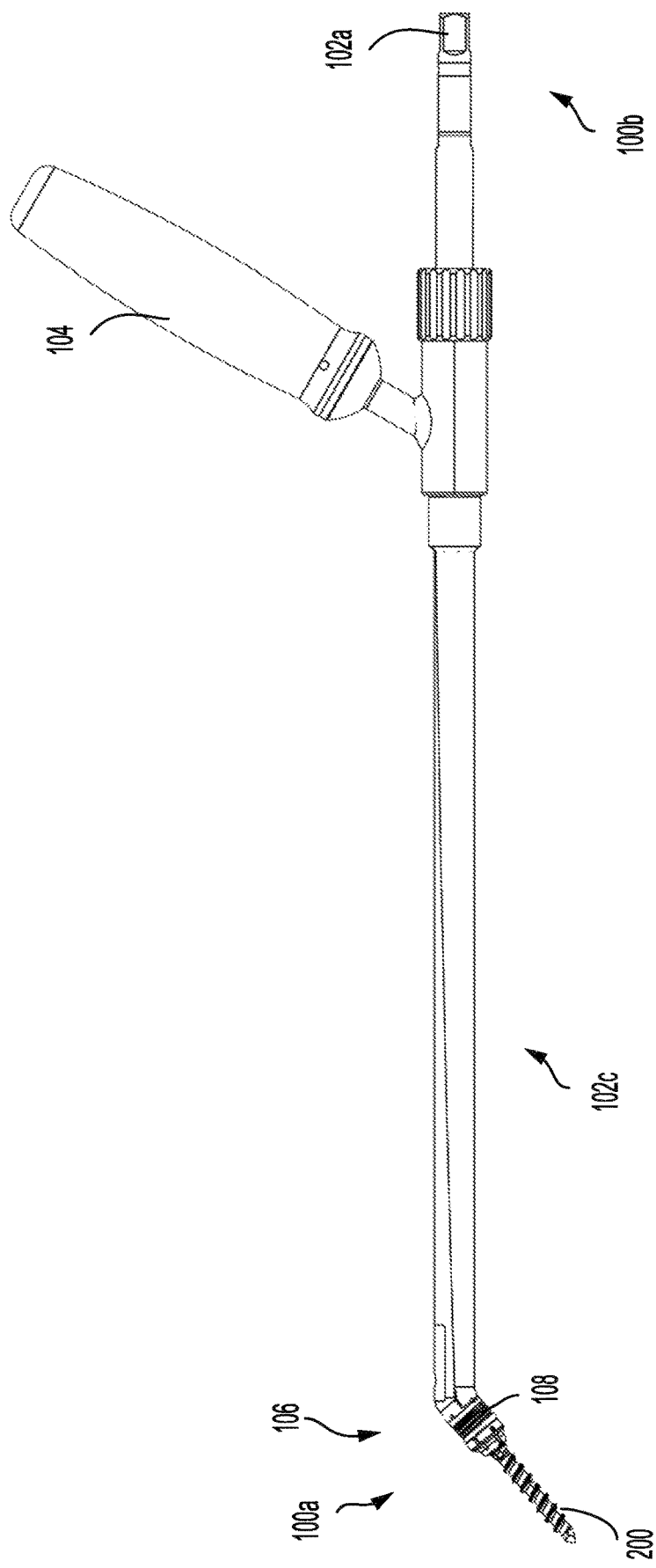
FIG. 2 is a side view of an example screwdriver in accordance with the principles of the present disclosure.

Referring generally to FIGS. 1-4B an example screwdriver 100 is illustrated. FIG. 1 is a perspective view of an example screwdriver 100 and FIG. 2 is a side view of the example screwdriver 100. Screwdriver 100 may include a proximal end 100a and a distal end 100b. Screwdriver 100 may also include a drive shaft 102, a positioning handle 104, a tip portion 106, a retaining cap 108, and a housing 110, among other things. Drive shaft 102 may be configured to connect and disconnect with various types of drivers including manually operated handles and mechanically powered drive means that may be of a ratcheting or non-ratcheting type and which will be discussed in further detail below (see, e.g., FIGS. 19-22). For example, drive shaft 102 may include a drive portion 102a disposed at a distal end thereof, a drive end 102b disposed at a proximal end thereof, and a main drive shaft portion 102c extending in a longitudinal direction through a housing 110. Drive portion 102a may comprise a variety of drive interfaces for coupling and uncoupling with various manually operated ratcheting handles and powered drivers. Drive shaft 102 may freely rotate inside of housing 110 to transfer rotational force applied at the drive portion 102a to drive end 102b. Positioning handle 104 may be securely held in place while drive shaft 102 freely rotates within housing 110. Positioning handle 104 may be configured to assist with maintaining and controlling the screwdriver 100, e.g., in view of torque transmitted through drive shaft and the corresponding resultant return forces. At least one advantage of positioning handle 104 is that a surgeon may have greater control maintaining screwdriver 100 in a desired position while driving a bone screw 200. For example, when installing a bone screw 200 into the anatomy of a patient a return force may apply a rotational force against the screwdriver 100 and a surgeon may be able to maintain the screwdriver 100 in the desired position.

Figure 11:
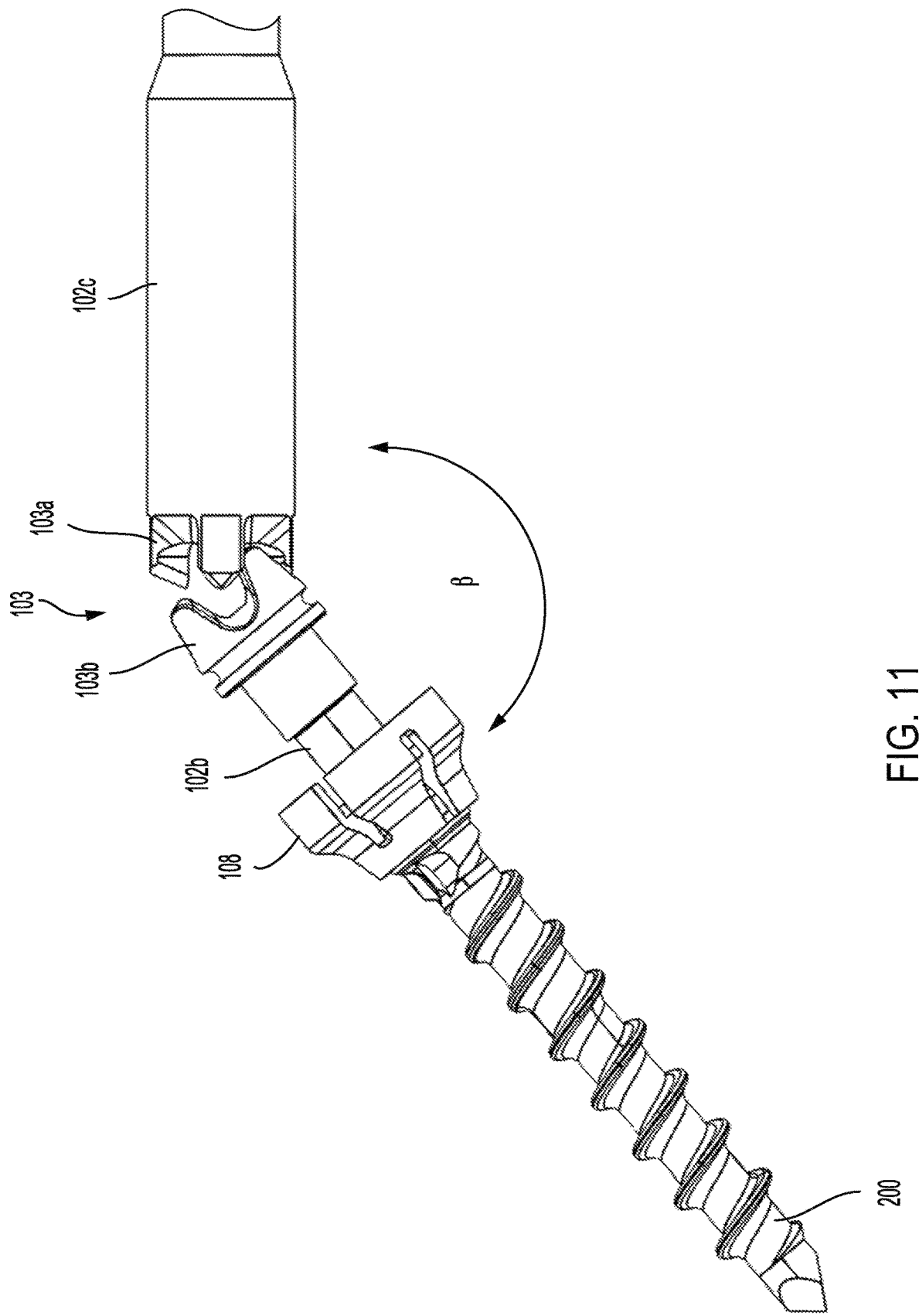
FIG. 11 is a side view of a gear mechanism in accordance with the principles of the present disclosure.
Figure 12A:
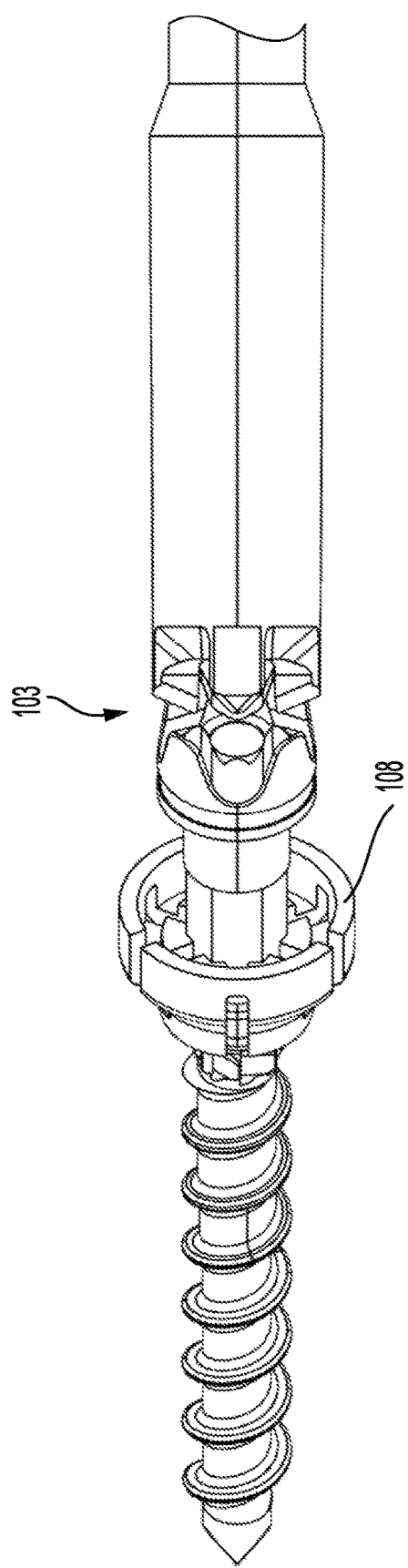
FIG. 12A is a top view of a gear mechanism in accordance with the principles of the present disclosure.
Figure 12B:
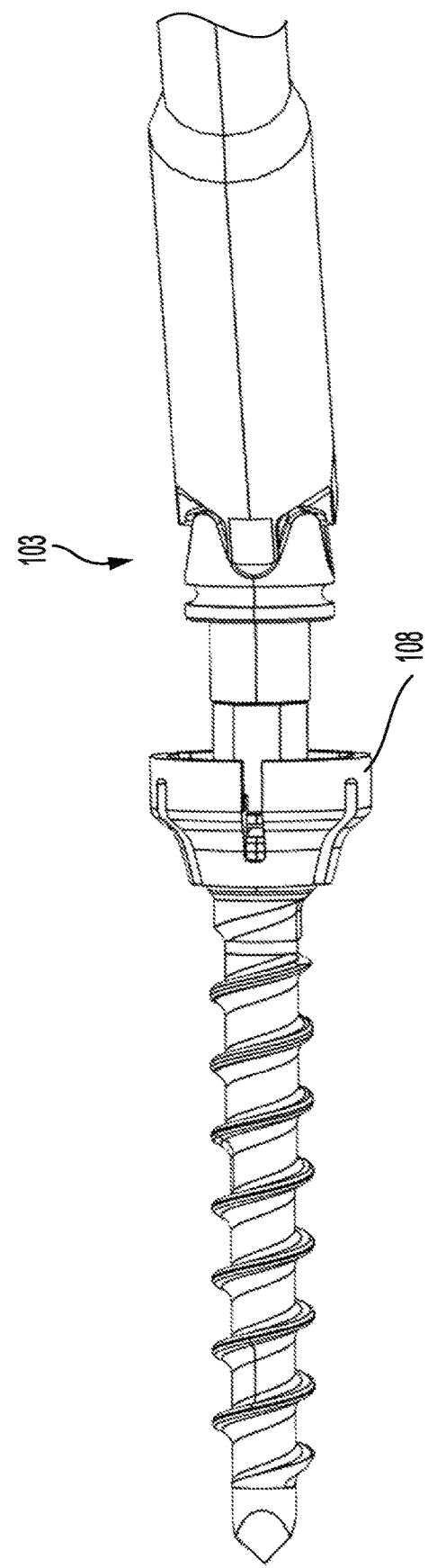
FIG. 12B is a bottom view of a gear mechanism in accordance with the principles of the present disclosure.

FIG. 3 is a magnified view of the tip portion 106 of an example screwdriver 100 in accordance with the principles of the present disclosure. Tip portion 106 may be angled at a degree β (Beta) with respect to a longitudinal direction of housing 110 and/or drive shaft portion 102c (see FIG. 11). In some embodiments, tip portion 106 is angled such that the degree β corresponds to the desired inclination of bone screw 200. In some embodiments, the degree β corresponds to an inclination of a bone screw aperture of a medical plate or medical device, e.g., medical device 1000 is a spinal implant including at least one bone screw aperture 1002 (see FIG. 23). For example, tip portion 106 may be inclined about 20°-60°, more particularly about 30°-50°, and even more particularly about 40°-45°, with respect to a longitudinal direction of housing 110. However, it shall be understood that tip portion 106 may be angled at any degree β Similarly, bone screw apertures 1002 may be angled at any degree with respect to endplates 1010, 1020 and tip portion 106 may be angled at a corresponding degree β to facilitate the installation of bone screw 200 therein. This angled arrangement may be advantageous for driving bone screw 200 while medical device 1000 is positioned between adjacent vertebral bodies. Furthermore, this angled arrangement may be advantageous to avoid anatomical landmarks and features such as the pelvic ring, rib cage, and iliac crest, of a patient, for example.

Figure 4A:
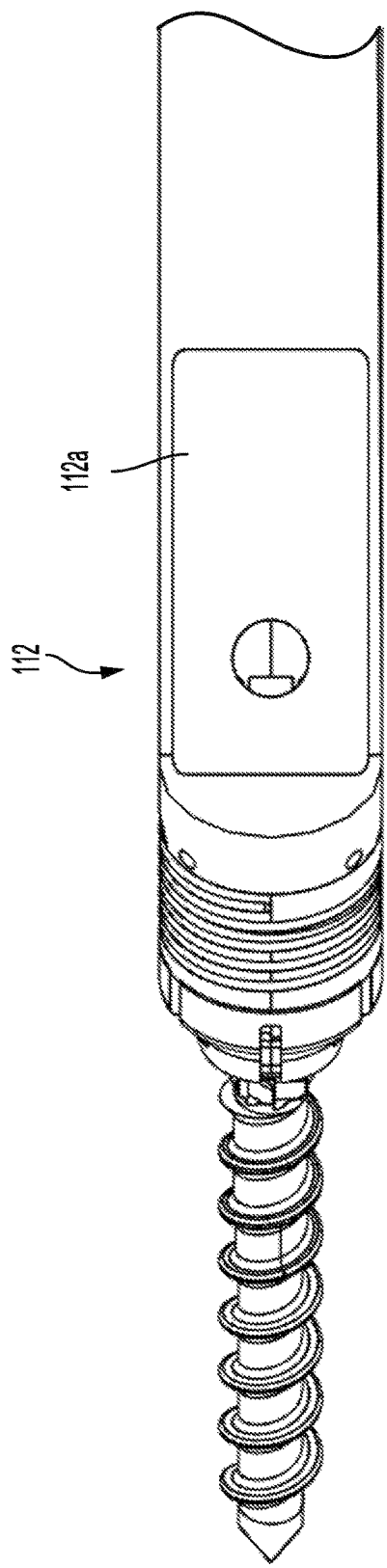
FIG. 4A is a top down view of a flushing portion of an example screwdriver in accordance with the principles of the present disclosure.
Figure 4B:
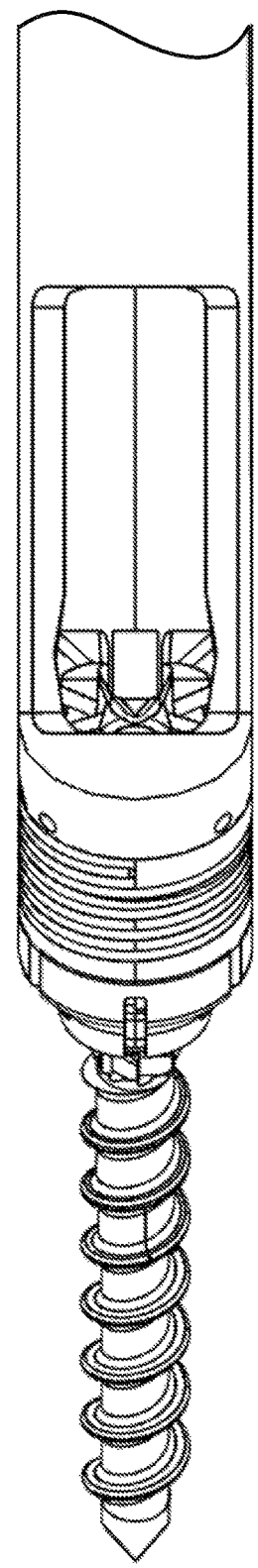
FIG. 4B is a top down view of a flushing portion of an example screwdriver with partially removed parts for ease of understanding in accordance with the principles of the present disclosure.

FIGS. 4A and 4B illustrate an example screwdriver 100 that may include a flushing hole 112 having a flushing path to clean the tip portion 106, or to lubricate the mechanism. For example, as shown in FIG. 4A a flushing hole 112 is shown, and in FIG. 4B a cover 112a is removed to illustrate the flushing path. Flushing hole 112 may be advantageous for cleaning the interior orifices of tip portion 106.

Figure 5:
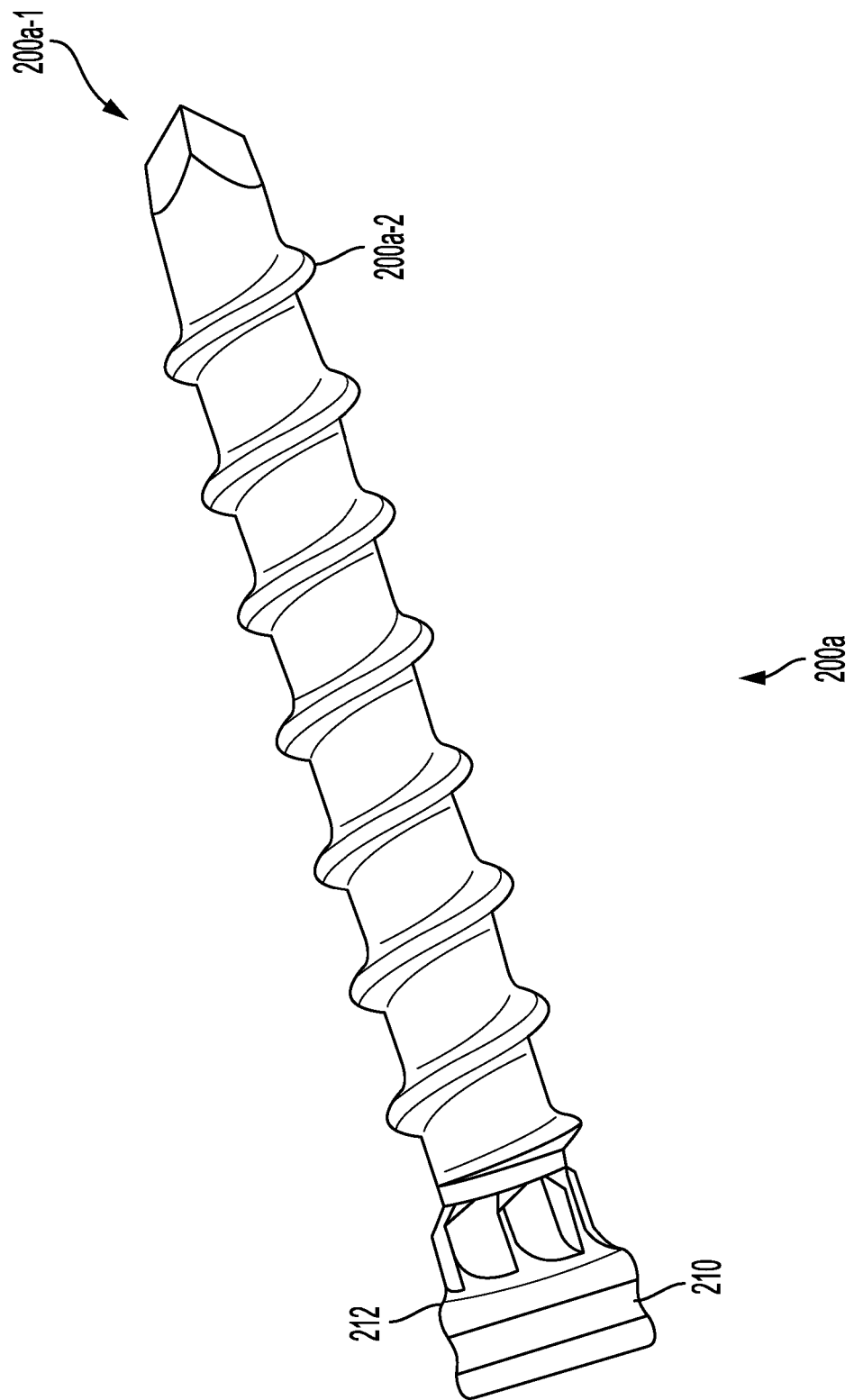
FIG. 5 is a perspective view of an example bone screw suitable for use with disclosed embodiments in accordance with the principles of the present disclosure.
Figure 6:
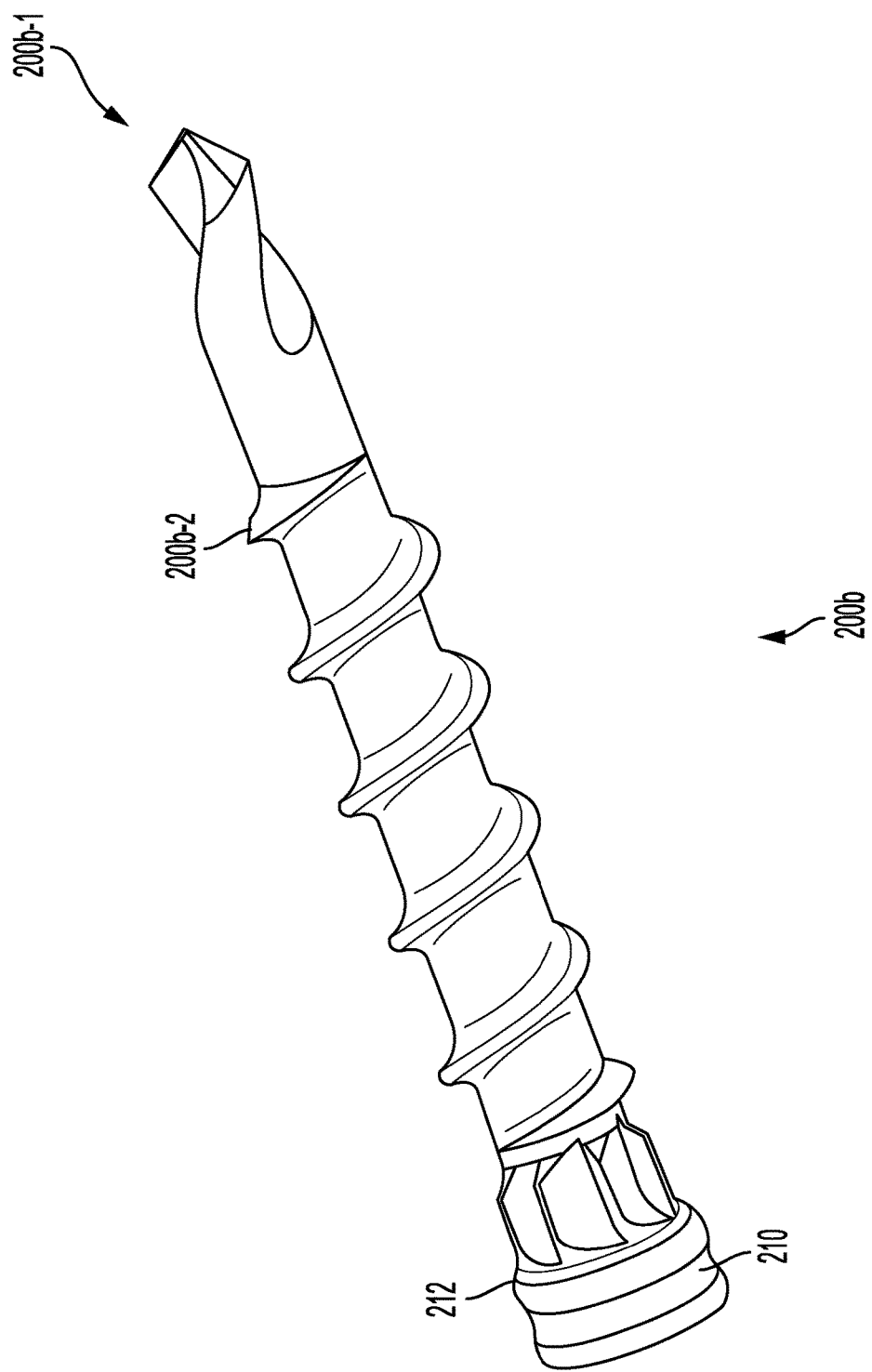
FIG. 6 is a perspective view of an example bone screw suitable for use with disclosed embodiments in accordance with the principles of the present disclosure.
Figure 7:
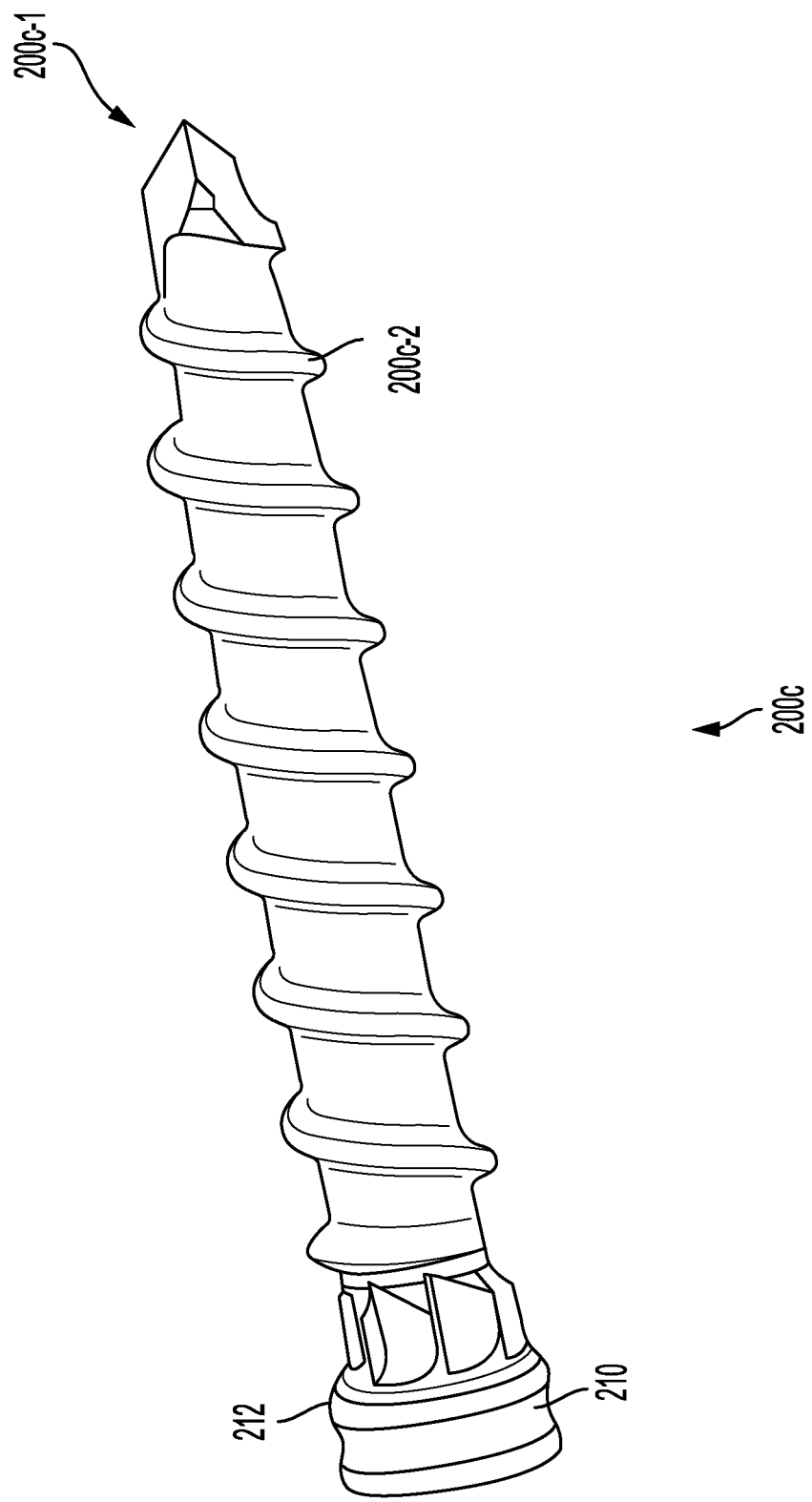
FIG. 7 is a perspective view of an example bone screw suitable for use with disclosed embodiments in accordance with the principles of the present disclosure.

FIG. 5 is a perspective view of an example trocar tip bone screw 200a suitable for use with disclosed embodiments in accordance with the principles of the present disclosure. FIG. 6 is a perspective view of an example flutes or fluted tip bone screw 200b suitable for use with disclosed embodiments in accordance with the principles of the present disclosure. FIG. 7 is a perspective view of an example speed bone screw suitable for use with disclosed embodiments in accordance with the principles of the present disclosure. Each bone screw 200a, 200b, 200c may be referred to throughout the disclosure generally as bone screw 200 to refer to bone screws generally and including any of the example bone screws 200a, 200b, 200c. Additionally, each bone screw 200a, 200b, 200c may have a single or multiple thread pitch and sizing that corresponds to a size of bone screw aperture 1002, for example.

Trocar tip bone screw 200a includes an angled tip portion 200a-1 and a thread pattern including threads 200a-2. Threads 200a-2 may be spaced back from angled tip portion 200a-1 which may facilitate with aligning bone screw 200a with bone screw aperture 1002. For example, in some embodiments, threads 200a-2 are spaced back about 3 mm from angled tip portion 200a-1. Fluted tip bone screw 200b includes a cutting tip 200b-1 and a thread pattern included threads 200b-2. Cutting tip 200b-1 may extend a relatively long distance from the beginning of threads 200b-2 such that the cutting tip 200b-1 may pre-drill into an anatomical feature or tissue such as a bone or an adjacent vertebral body before the threads 200b-2 engage with bone screw aperture 1002. For example, in some embodiments, threads 200b-2 are spaced back about 8 mm from cutting tip 200b-1. Speed bone screw 200c includes a conical tip 200c-1 and a thread pattern including threads 200c-2. Different from trocar tip bone screw 200a and fluted tip bone screw 200b, threads 200c-2 of speed bone screw 200c may begin immediately adjacent conical tip 200c-1.

Each of the example bone screws 200a, 200b, 200c may be configured for use with example screwdrivers 100 disclosed herein. Additionally, each of the example bone screws 200a, 200b, 200c may include an indent 210 spanning the circumference of the head portion and an adjacent edge portion 212 spanning the circumference of the head portion. In some embodiments, indent 210 may be defined by an arcuate circumferential groove that spans the circumference of a midsection of the head of bone screw 200. Additionally, in some embodiments, edge portion 212 may be defined by an arcuate or chamfered edge spanning the circumference of the head portion adjacent the threads of bone screw 200. The indent 210 and/or edge portion 212 may be advantageous for clipping and/or retaining bone screws 200a, 200b, 200c in screwdriver 100, as will be explained in more detail below.

Figure 8:
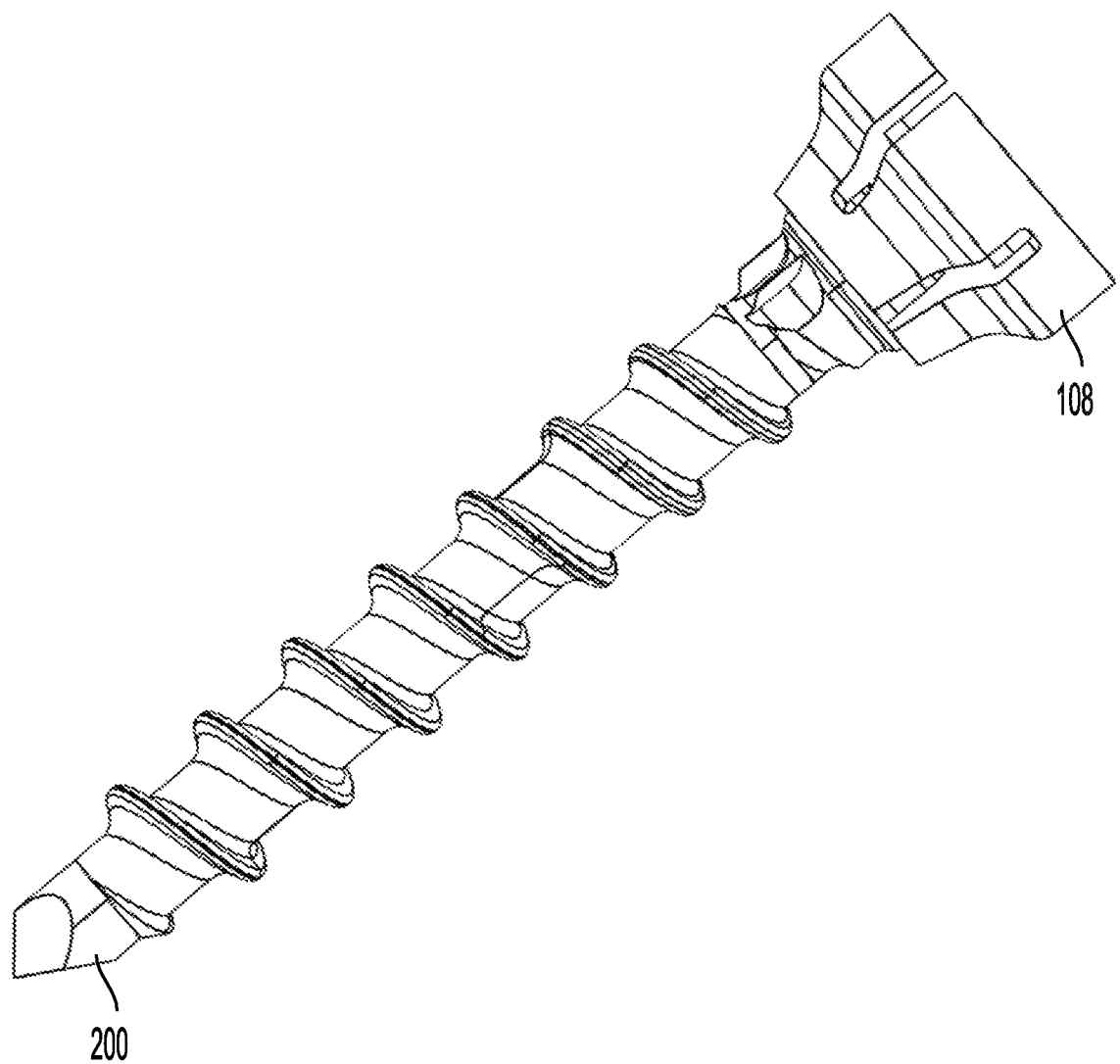
FIG. 8 is a perspective view of an example bone screw coupled to a retaining cap in accordance with the principles of the present disclosure.
Figure 9A:
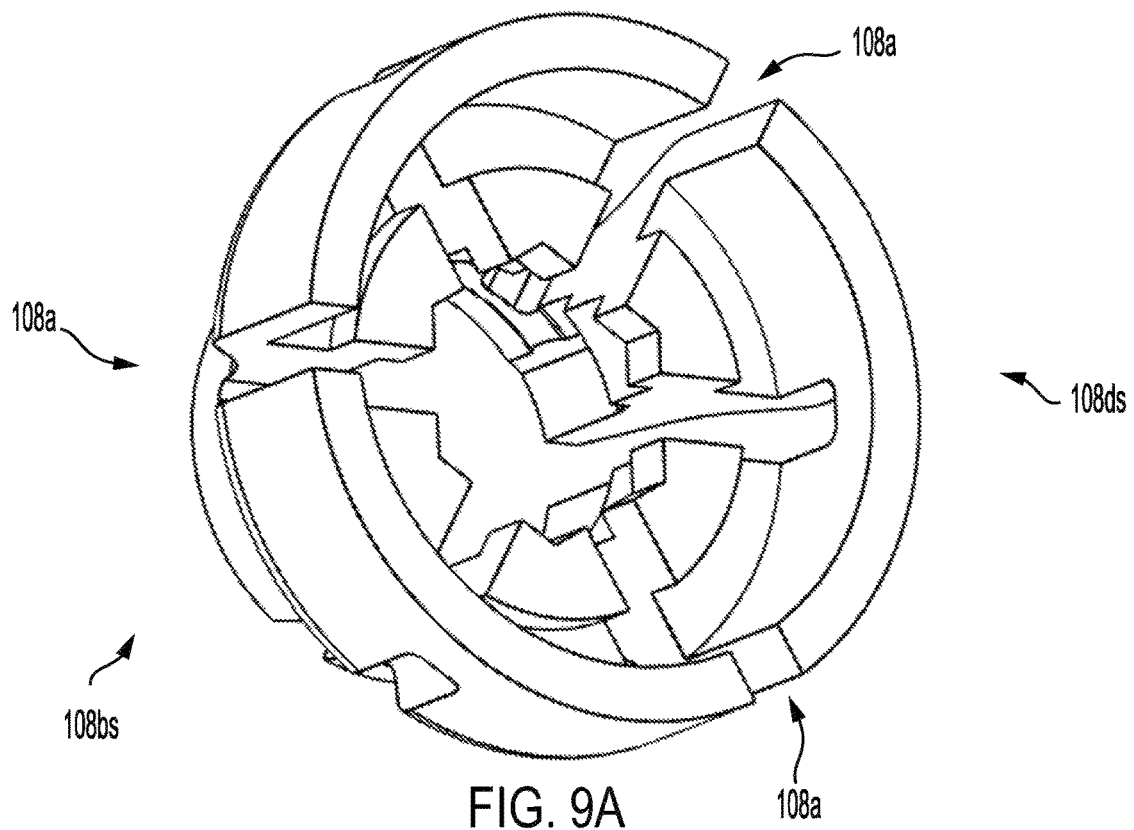
FIG. 9A is a perspective view of a retaining cap viewed from a drive shaft connecting side in accordance with the principles of the present disclosure.
Figure 9B:
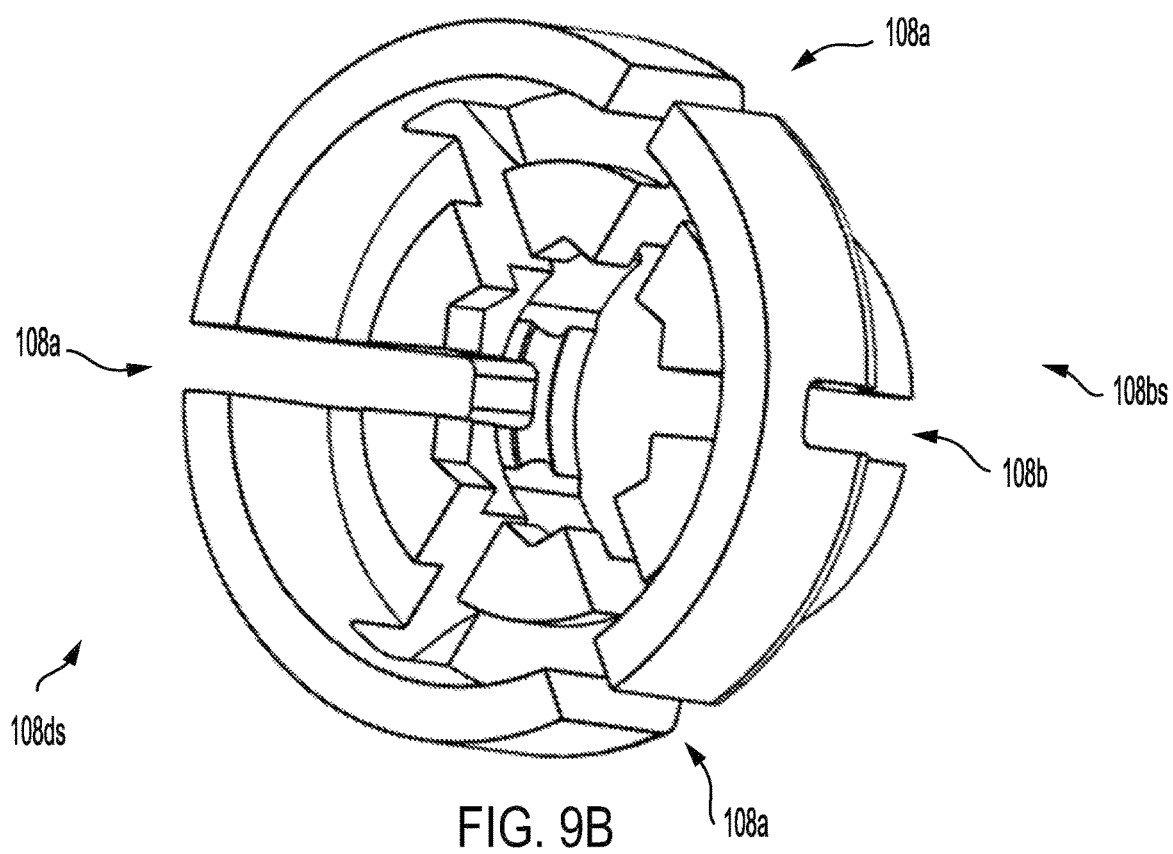
FIG. 9B is an alternate perspective view of a retaining cap viewed from a drive shaft connecting side in accordance with the principles of the present disclosure.
Figure 10A:
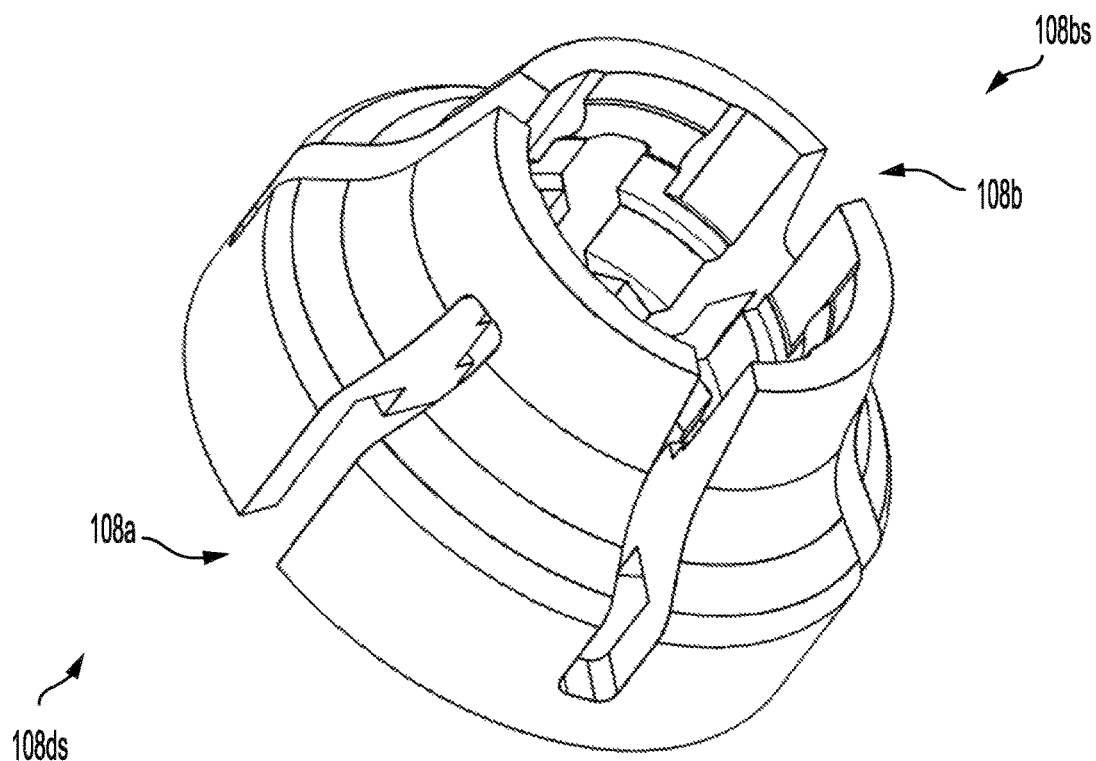
FIG. 10A is a perspective view of a retaining cap viewed from a bone screw retaining side in accordance with the principles of the present disclosure.
Figure 10B:
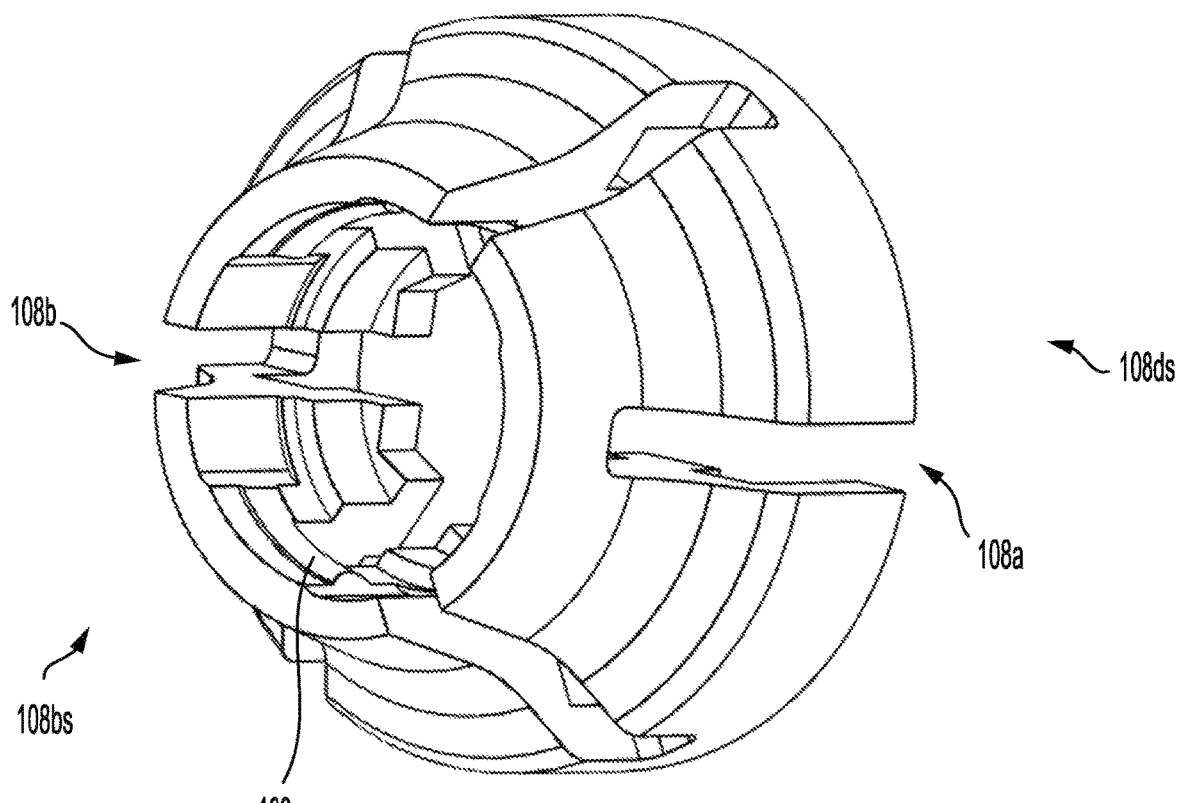
FIG. 10B is a perspective view of a retaining cap viewed from a bone screw retaining side in accordance with the principles of the present disclosure.

FIG. 8 is a perspective view of an example bone screw 200 coupled to and retained by an example retaining cap 108 in accordance with the principles of the present disclosure. FIGS. 9A and 9B are perspective views of retaining cap 108 viewed from a drive shaft connecting side 108ds in accordance with the principles of the present disclosure and FIGS. 10A and 10B are perspective views of retaining cap 108 viewed from a bone screw connecting side 108bs in accordance with the principles of the present disclosure. Retaining cap 108 may be composed of elastomeric materials, thermoplastic materials, metallic materials, and various combinations thereof. In one embodiment, retaining cap 108 is composed of metallic material, e.g., stainless steel and/or titanium. In another embodiment, retaining cap 108 is composed of elastomeric material, e.g., rubber and/or high-density rubber. In another embodiment, retaining cap 108 is composed of thermoplastic material, e.g., Polyether ether ketone (PEEK) and/or other organic thermoplastic polymers in, e.g., the polyaryletherketone (PAEK) family. In another embodiment, retaining cap 108 is composed of polyphenylsulfone (PPSU), also referred to as Radel by those with skill in the art.

In the example embodiment, the drive shaft connecting side 108ds includes a plurality of first aperture channels 108a and the bone screw connecting side 108bs includes a plurality of second aperture channels 108b. In some embodiments, a circumference of the drive shaft connecting side 108ds may be greater than a circumference of the bone screw connecting side 108bs. First aperture channels 108a may take the shape of a slit or narrow void extending from the drive shaft connecting side 108ds towards the bone screw connecting side 108bs. Second aperture channels 108b may take the shape of a slit or narrow void extending from the drive shaft connecting side 108ds towards the bone screw connecting side 108bs. In the example embodiment, three (3) first aperture channels 108a and three (3) second aperture channels 108b are illustrated, although retaining cap 108 may have any number of aperture channels 108a, 108b. For example, other embodiments may include two aperture channels 108a, 108b, four aperture channels 108a, 108b, or five aperture channels 108a, 108b, for example. In the disclosed embodiment, first aperture channels 108a are spaced apart symmetrically from one another around the circumference of the drive shaft connecting side 108ds Similarly, second aperture channels 108*b* are spaced apart symmetrically from one another around the circumference of the bone screw connecting side 108*bs*. Furthermore, each first aperture channel 108*a* may be spaced between two immediately adjacent second aperture channels 108*b* at a midpoint distance between the two immediately adjacent second aperture channels 108*b* Similarly, each second aperture channel 108*b* may be spaced between two immediately adjacent first aperture channels 108*a* at a midpoint distance between the two immediately adjacent first aperture channels 108*a*. For example, as illustrated the aperture channels 108*a*, 108*b* are symmetrically disposed around the retaining cap 108 on opposite sides thereof with respect to one another. Additionally, each aperture channel may extend from about 10%-95% of the length of retaining cap 108 and the length and width of each aperture channel may be adjusted to increase or decrease the desired flexibility of retaining cap 108.

Additionally, retaining cap 108 may include a plurality of bumps 108*c* at a bone screw connecting side 108*bs*. Bumps 108*c* may be inset from an outermost surface of the bone screw connecting side 108*bs* on an interior thereof. Bumps 108*c* may extend along the internal surface of retaining cap 108 at the bone screw connecting side 108*bs*. In the disclosed embodiment, three bumps 108*c* are illustrated although there may be more or less, for example two bumps 108*c*, four bumps 108*c*, or five bumps 108*c*. In the disclosed embodiment, the number of bumps 108*c* may correspond to the number of aperture channels 108*b*. For example, in the disclosed embodiment there may be three aperture channels 108*b* and three bumps 108*c* where each bump is disposed symmetrically between adjacent aperture channels 108*b*. Furthermore, a curved distance along the interior circumference of bone screw connecting side 108*bs* between adjacent aperture channels 108*b* may be greater than a curved distance (length) of bumps 108*c*. For example, in some embodiments, a circumferential length of bumps 108*c* may range from about 25%-75% of the circumferential distance between adjacent aperture channels 108*b*. Additionally, when viewed in cross section, bump 108*c* may be shaped like an arc of a circle or cylinder. However, in other embodiments, bump 108*c* may have alternate shapes such as prismoidal, polygonal, conical, etc. In the disclosed embodiment, bump 108*c* may have a cross sectional shape generally corresponding to indent 210. Accordingly, those with skill in the art will recognize that bump 108*c* and indent 210 may take any shape and that it in some embodiments it may be advantageous that their shapes correspond with one another.

At least one advantage of the geometrical arrangement of aperture channels 108*a*, 108*b* is that they may allow the retaining cap 108 to deform, at least partly, to couple/uncouple with the head of a bone screw 200 and/or drive end 102*b*. For example, a bone screw 200 may be inserted into the retaining cap 108 and clipped or retained by the retaining cap 108 by inserting the head of the bone screw 200 into the retaining cap 108 with a sufficient force, i.e., a clipping force. When inserting the head of the bone screw 200 into the retaining cap 108, the retaining cap 108 may deform, at least partly, consistent with the above disclosure when clipping the bone screw 200. In some embodiments, a clipping force may be about 1 N-6 N (Newtons), more particularly about 2 N-4 N, and even more particularly about 2.5 N Similarly, the retaining cap 108 may be attached to drive end 102*b*. For example, retaining cap 108 may be attached to drive end 102*b* with an attachment force of about 10 N-40 N, more particularly about 15 N-30 N, and even more particularly about 20 N. In this way, retaining cap 108 may be considered elastic although not necessarily composed of an elastomeric material.

A particular advantage of a flexible retaining cap 108 as described herein is that it may (1) retain a bone screw 200 therein with a clipping force and (2) automatically release the bone screw 200 when it is sufficiently installed or anchored. For example, during an installation or driving procedure, a bone screw 200 may be retained in the retaining cap 108 until the bone screw 200 is sufficiently installed in a target object or surgical site such that a sufficient extraction force pulls the bone screw 200 from the retaining cap 108, i.e., the extraction force exceeds the clipping or retaining force. For example, when driving the bone screw 200 into the target object or surgical site, the retaining cap 108 may deform, at least partly, consistent with the above disclosure when releasing the bone screw 200. In some embodiments, an extraction force may be about 2 N-30 N, more particularly about 10 N-20 N, and even more particularly about 15 N. In some embodiments, a ratio of the clipping force to the extraction force may about 1:15, more particularly about 1:10, and even more particularly about 1:6. For example, in at least one embodiment the retaining cap 108 is composed of a PEEK material and the clipping force is about 2.5 N and the extraction force is about 15 N.

Referring generally to FIGS. 11-13B, an example gear mechanism 103 may be provided. Gear mechanism 103 may include worm gears, beveled gears, miter gears, planetary gears, sliding gears, helical or spiral gears, gear coupling parts, pawls, having teeth of various sizing and shapes for directing a rotation of the drive shaft 102 to drive end 102*b*. For example, applying a rotation force at drive portion 102*a* may apply an equal or substantially equal rotation force at drive end 102*b* because the gear mechanism 103 may redirect the rotation force. As illustrated, gear mechanism 103 may include a first group of teeth 103*a* that are meshed with a second group of teeth 103*b*. In the example embodiment, the first group of teeth 103*a* includes fourth teeth and the second group of teeth 103*b* includes four teeth although the total number of teeth may be more or less. Those with skill in the art will readily appreciate that the particular geometry and number of teeth 103*a*, 103*b* may be modified to accommodate any particular angle β (see FIG. 3). Additionally, in some embodiments, gear mechanism 103 may be designed to provide a mechanical advantage, such increasing or lowering the speed of rotation. For example, when a ratio of teeth sizing of teeth 103*a*, 103*b* is inferior or superior with respect to the other.

Figure 13A:
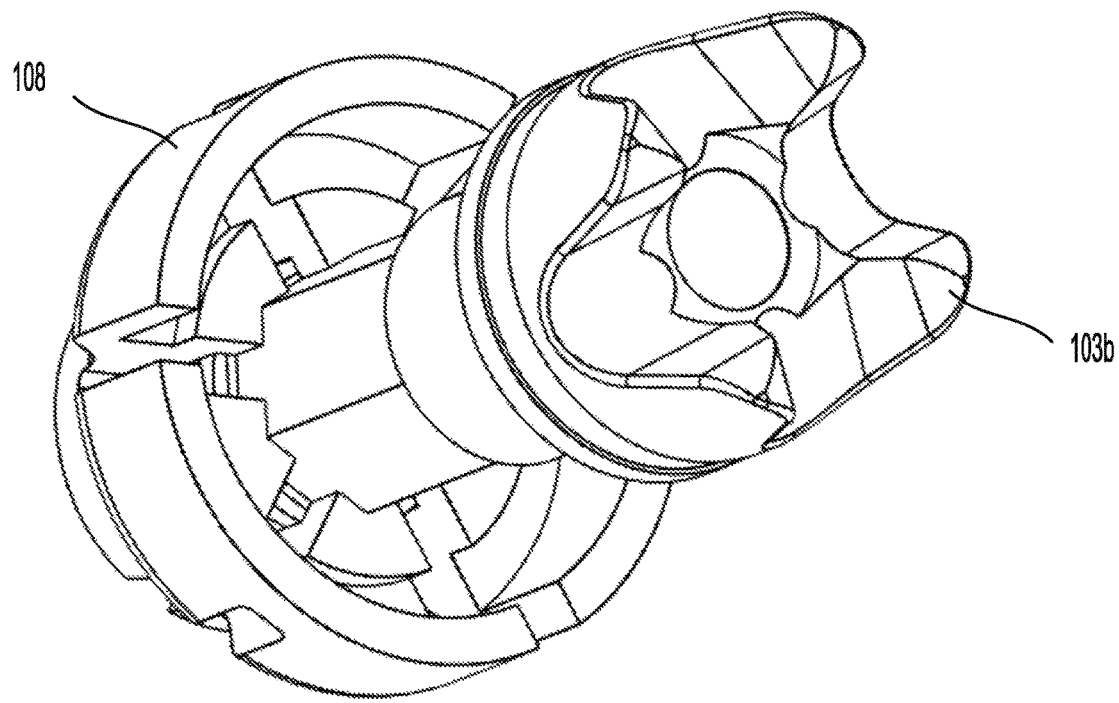
FIG. 13A is a perspective view of a first portion of a gear mechanism and a retaining cap in accordance with the principles of the present disclosure.
Figure 13B:
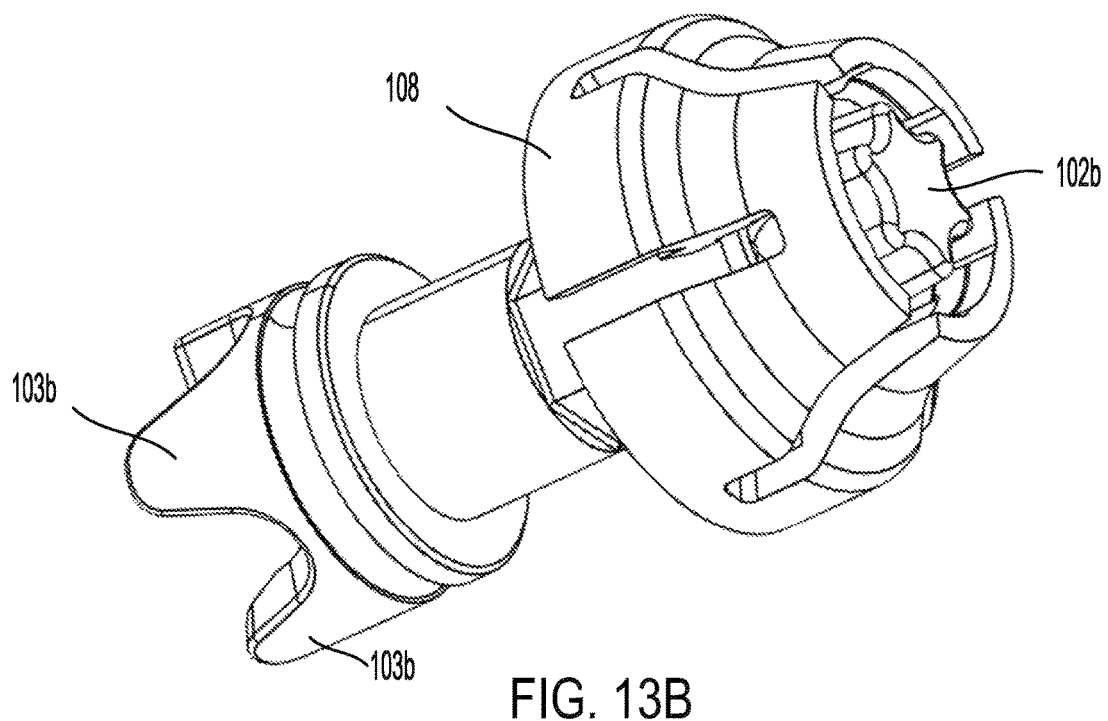
FIG. 13B is a perspective view of a first portion of a gear mechanism and a retaining cap in accordance with the principles of the present disclosure.

As illustrated best in FIG. 13B, drive end 102*b* may disposed in an internal cavity of retaining cap 108 such that it may mate with a head of a corresponding bone screw 200. Additionally, the retaining cap 108 may be coupled to drive end 102*b* in such a way that it will also rotate when drive end 102*b* rotates. In the illustrated embodiment, drive end 102*b* includes a torx head driver configuration, although other designs are contemplated, including star or hexalobular configurations. For example, the drive end 102*b* may resemble the geometry of the tip of a torx driver, hex driver, phillips driver, square head driver, hexalobular driver, polygonal driver, or the like. In at least one embodiment, a Torx T20 size driver may be used.

Figure 14:
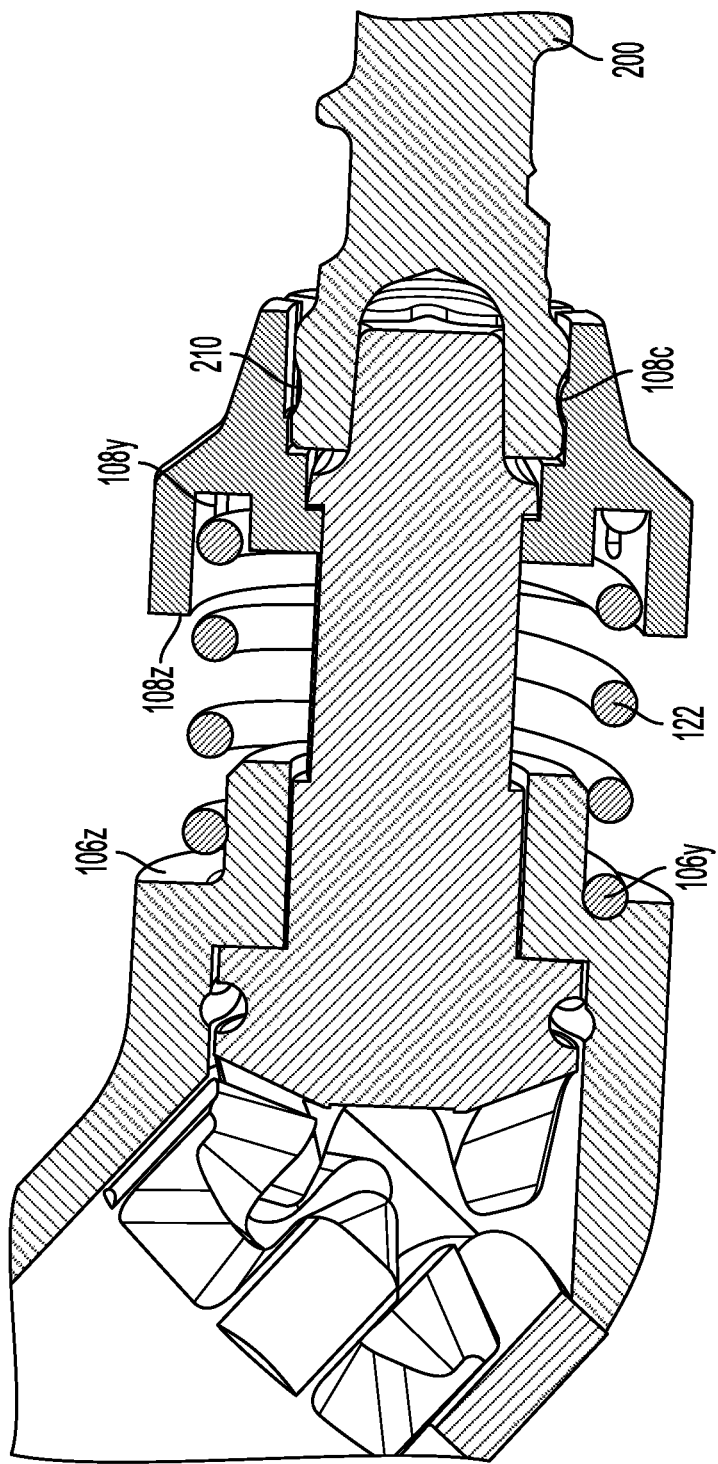
FIG. 14 is a cross section view of a tip portion of an example screwdriver in accordance with the principles of the present disclosure.
Figure 15:
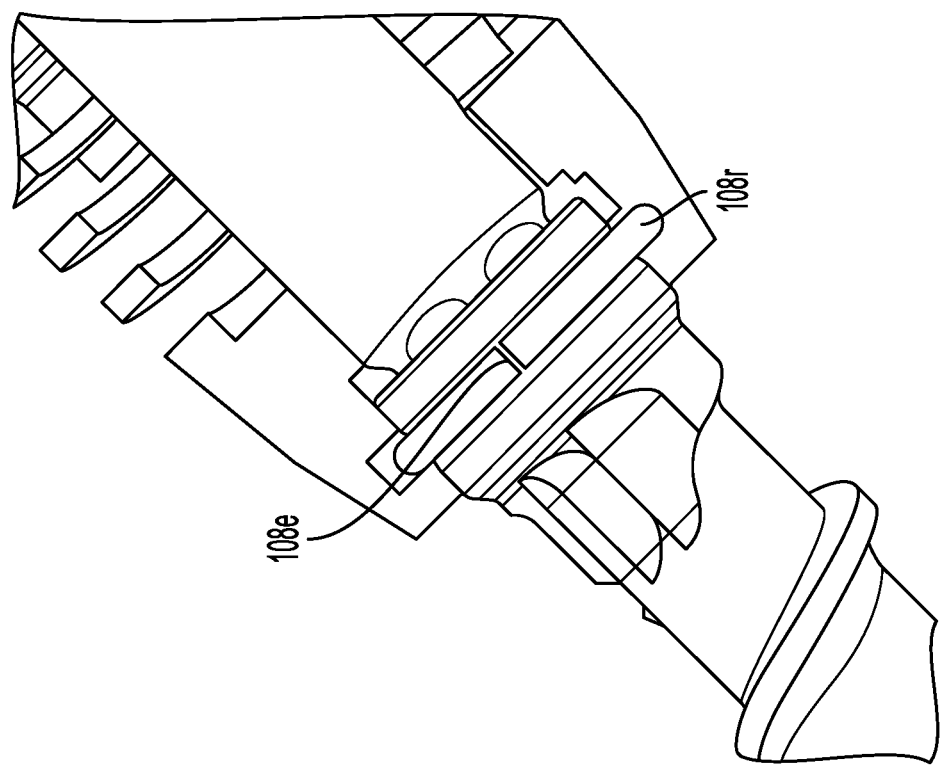
FIG. 15 is a removed parts view of a tip portion of an example screwdriver in accordance with the principles of the present disclosure.
Figure 16:
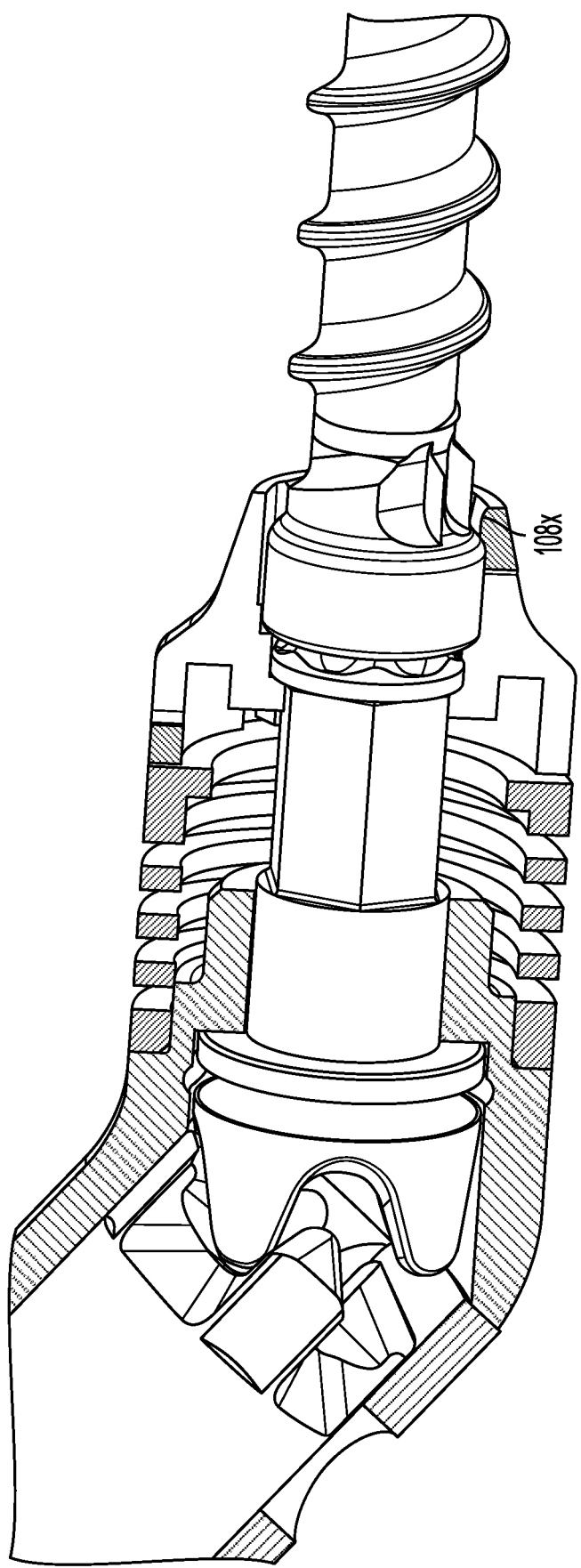
FIG. 16 is a removed parts view of an example gear mechanism in accordance with the principles of the present disclosure.
Figure 17:
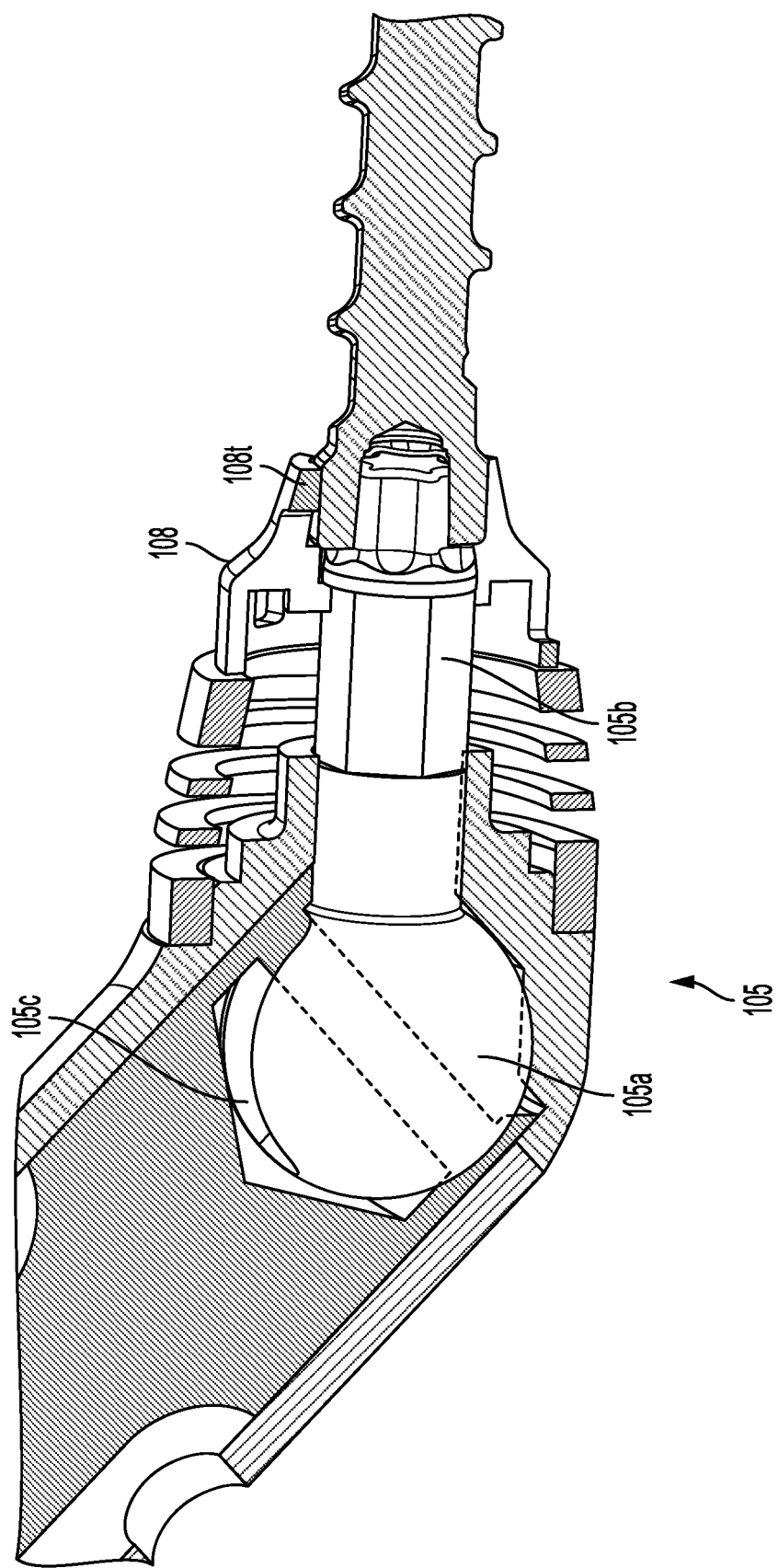
FIG. 17 is a removed parts view of an alternate example gear mechanism in accordance with the principles of the present disclosure.
Figure 18A:
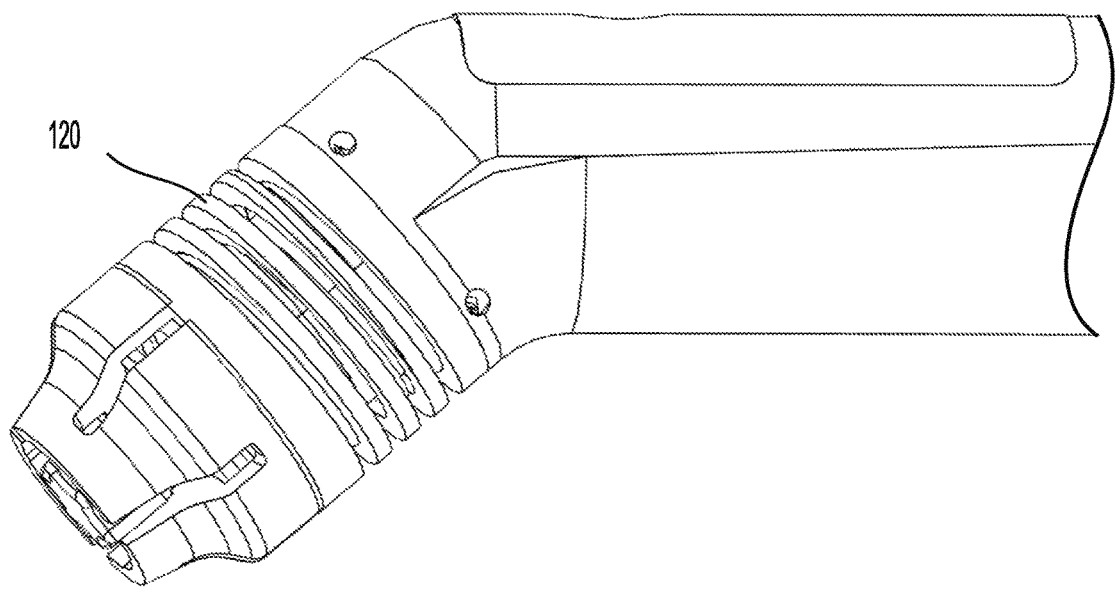
FIG. 18A is a side view of a tip portion of an example screwdriver in accordance with the principles of the present disclosure.
Figure 18B:
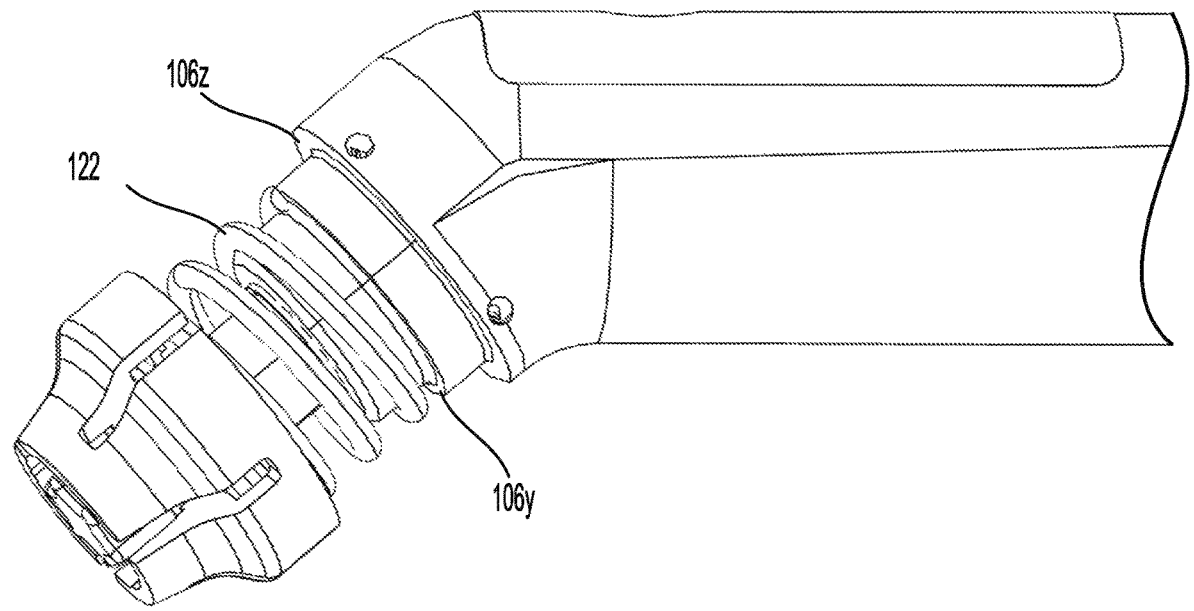
FIG. 18B is a side view of a tip portion of an example screwdriver with compression spring in accordance with the principles of the present disclosure.

Referring generally to FIGS. 14-18B a tip portion 106 of an example screwdriver 100 may be illustrated. FIG. 14 is a cross section view of a tip portion 106 and FIG. 15 is a removed parts view of a tip portion 106 of an example screwdriver 100 in accordance with the principles of the present disclosure. FIG. 16 is a removed parts view of an example gear mechanism 103 in accordance with the principles of the present disclosure and FIG. 17 is a removed parts view of an alternate example gear mechanism 103 in accordance with the principles of the present disclosure. FIG. 18A is a side view of an example tip portion 106 in a fully assembled condition and FIG. 18B is a side view of an example tip portion 106 in accordance with the principles of the present disclosure.

In some embodiments, retaining cap 108 may include at least one retaining feature such as bump 108c, for example. Additionally, some example bone screws 200 may include an indent 210 (see FIGS. 5-7). In a head on view, the indent 210 may be defined by a radius of a circle that is slightly less than a radius defining a tip portion of the head of bone screw 200. The retaining bump 108c may have a curved surface profile including a width and depth that corresponds to the width and depth of the indent 210. Additionally, when viewed in a cross sectional view, retaining bump 108c may be seated within indent 210. In disclosed embodiments, tip portion 106 may include a first spring 120 and a second spring 122. However, in some embodiments, only one of first spring 120 or second spring 122 may be provided. Example springs 120, 122 may be referred to as industrial compression springs, machined springs, coil springs, and/or helical springs. First spring 120 may have outside surfaces that are flush with the adjacent surfaces, i.e., outside surfaces of retaining cap 108 and tip portion 106 (see FIG. 18A). For example, first spring 120 may act against a bearing surface 108z of retaining cap 108 and a bearing surface 106z of tip portion 106 (see FIG. 14 and FIGS. 18A-18B). Second spring 122 may be disposed within a central cavity of first spring 120, i.e., second spring 122 may be surrounded by first spring 120. For example, second spring 122 may act against corresponding inset radial surfaces of retaining cap 108 and tip portion 106 that are disposed and inset radially from the surfaces that first spring 120 acts against. For example, second spring 122 may act against channel 108y of retaining cap 108 and bearing surface 106y of tip portion 106. In some embodiments, channel 108y may extend circumferentially around an interior of retaining cap 108 that is radially inset from the outside surface of retaining cap 108. Additionally, second spring 122 may act against a portion of bearing surface 106y that is radially inset from the portion of bearing surface 106z that contacts first spring 120 (see FIG. 14). Stated another way, first spring 120 may act against a radially outset surface and second spring 122 may act against a radially inset surface, at least with respect to one another. Each of springs 120, 122 may have a relative stiffness of about 1 N/mm-6 N/mm, more particularly about 2 N/mm-4 N/mm, and even more particularly about 3.35 N/mm. In some embodiments, only the second spring 122 contributes a significant portion of the relative stiffness ranges provided above and the first spring 120 may have a negligible contribution. In other embodiments, only the first spring 120 contributes a significant portion of the relative stiffness ranges provided above and the second spring 122 may have a negligible contribution. In other embodiments still, the sum of the stiffness of the first and second springs 120, 122 may be additive such that the combined stiffness of the first and second springs 120, 122 may be within the stiffness ranges provided above. At least one advantage of the first and/or second springs 120, 122 is that they may facilitate the clipping of a bone screw 200 to retaining cap 108 and the extraction of the bone screw 200 from the retaining cap 108 in a progressive manner. For example, when driving a bone screw 200 into a target site, the first and/or second springs 120, 122 may compress when the bone screw 200 nears a fully anchored position helping to moderate the extraction force required to remove the bone screw 200 in a precise or controlled way, or at least a relatively more precise or controlled way relative to conventional screw drivers. For example still, the first and/or second springs 120, 122 may allow the retaining cap 108 to progressively release a bone screw 200 when it is inserted and installed into a cavity or target location in a similar way.

FIG. 15 illustrates an alternate embodiment showing the retaining cap 108 including a retaining ring 108r. Retaining ring 108r may be formed of the same or similar materials as previously disclosed with respect to retaining cap 108. In at least one embodiment, retaining ring 108r is formed of a metallic material and retaining cap 108 is formed of PEEK. Retaining ring 108r may have a generally toroidal shape or torus shape. The retaining ring 108r may have at least one expansion joint 108e that divides the retaining ring into separable spaced apart regions. The expansion joint 108e may allow the retaining ring 108r to expand radially when a bone screw 200 is insert into the retaining cap 108. For example, the retaining ring 108r may have an internal radius and an external radius and the internal radius may correspond to the radius of a head of a bone screw 200. In the disclosed embodiment, the internal radius of the retaining ring 108r may be slightly less than the radius of a head of a bone screw 200 and may expand radially when a bone screw 200 is insert therein. In the disclosed embodiment, bone screw 200 includes an indent 210 (see FIGS. 5-7). In a head on view, the indent 210 may be defined by a radius of a circle that is slightly less than a radius defining a tip portion of the head of bone screw 200. The retaining ring 108r may have an internal radius that corresponds to the radius of the indent 210. Additionally, when viewed in a cross sectional view, retaining ring 108r may have a diameter that corresponds to a depth of indent 210 and the retaining ring 108r may be half-seated within the indent 210. For example, when the retaining ring 108r is seated in the indent 210, about half of the retaining ring 108r extends above the indent 210 and the other half of retaining ring 108r is within indent 210. However, in other embodiments the retaining ring 108r may be fully seated or partially seated in indent 210, e.g., 100% seated, 75% seated, or 25% seated.

FIG. 16 illustrates an alternate embodiment where retaining cap 108 includes a protrusion 108x (or a lip portion). Protrusion 108x may be a rounded or arcuate protrusion that extends circumferentially around the inside of retaining cap 108. For example, when viewed in cross section, protrusion 108x may be defined by a radius that is relatively smaller than a radius of the head of bone screw 200. At least one advantage of protrusion 108x is that it may assist in retaining bone screw 200 inside of retaining cap 108. Furthermore, in some embodiments, protrusion 108x may serve a similar function and/or have similar functionality as bump 108c. At least one advantage to protrusion 108x is that conventional bone screws that do not include indent 210 may be safely retained and controllably released by retaining cap 108 similarly as explained above with respect to bump 108c. In some embodiments, retaining cap 108 may combine both bump 108c and protrusion 108x.

FIG. 17 illustrates an alternate embodiment including a joint mechanism 105 in lieu of gear mechanism 103. Joint mechanism 105 may be operable/drivable via drive shaft 102 in the same, similar, or substantially the same way as gear mechanism 103 as explained above. As illustrated in FIG. 17, joint mechanism 105 may include a spherical portion 105a that is rotatably seated in a spherical housing area of tip portion 106. Spherical portion 105a may be fixedly coupled to drive portion 105b and drive portion 105b may include an end portion configured for driving bone screw 200 in the same, similar, or substantially the same way as drive end 102b explained above. In the example embodiment, spherical portion 105a includes an aperture 105c such as a drilled out portion or slotted portion configured to receive drive shaft 102 therein, for example. Drive shaft 102 may extend into aperture 105c and couple with spherical portion 105a and/or drive portion 105b to transmit rotational movement from drive shaft 102 to bone screw 200. For example drive shaft 102 may extend into aperture 105c and couple with spherical portion 105a and/or drive portion 105b via a pin connection. At least one advantage of this structural arrangement is that the joint mechanism 105 may be configured such that it is adjustable to accommodate a range of various angles of inclination β of tip portion 106 with respect to housing 110. For example, joint mechanism 105 may enable a user selectable and greater operating range of various angles of inclination β. For example still, joint mechanism 105 may enable tip portion 106 to be adjustably inclined within a range of about 20°-60°, and more particularly about 30°-50 with respect to a longitudinal direction of housing 110. However, it shall be understood that in some embodiments the angle of inclination β may be fixed.

FIG. 17 also illustrates an alternate embodiment of retaining cap 108. In the disclosed embodiment, retaining cap 108 may include a tapered portion 108t. For example, the bone screw connecting side 108bs of retaining cap 108 may taper conically. For example still, when viewed in cross-section, a radius of tapered portion 108t may progressively decrease along retaining cap 108 to an outermost end thereof. It shall be understood that retaining cap 108 may include bump 108c, protrusion 108x, and/or tapered portion 108t and any combination thereof. Additionally, any of bump 108c, protrusion 108x, and/or tapered portion 108t may be referred to as a retaining contour or retaining feature in some embodiments.

Figure 19:
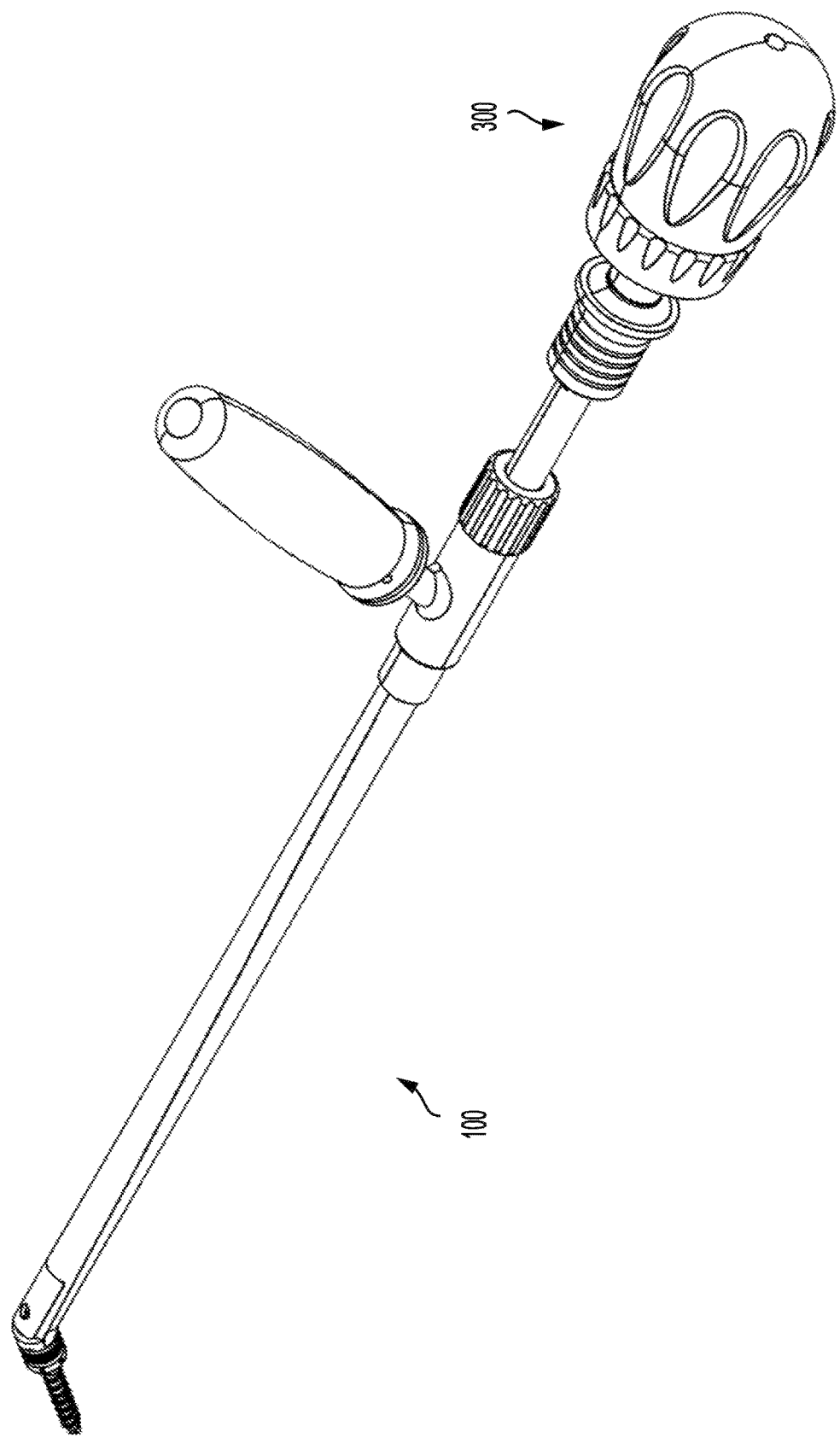
FIG. 19 is a perspective view of an example screwdriver coupled to a manual hand driver in accordance with the principles of the present disclosure.
Figure 20:
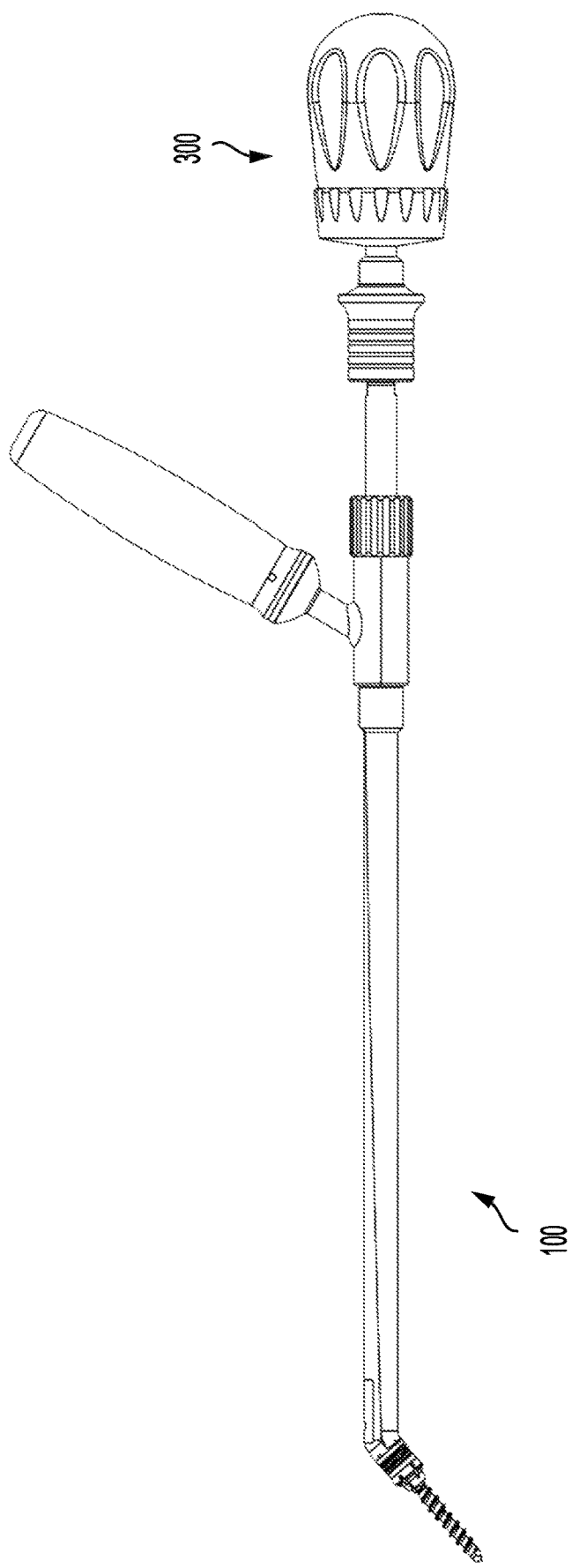
FIG. 20 is a side view of an example screwdriver coupled to a manual hand driver in accordance with the principles of the present disclosure.
Figure 21:
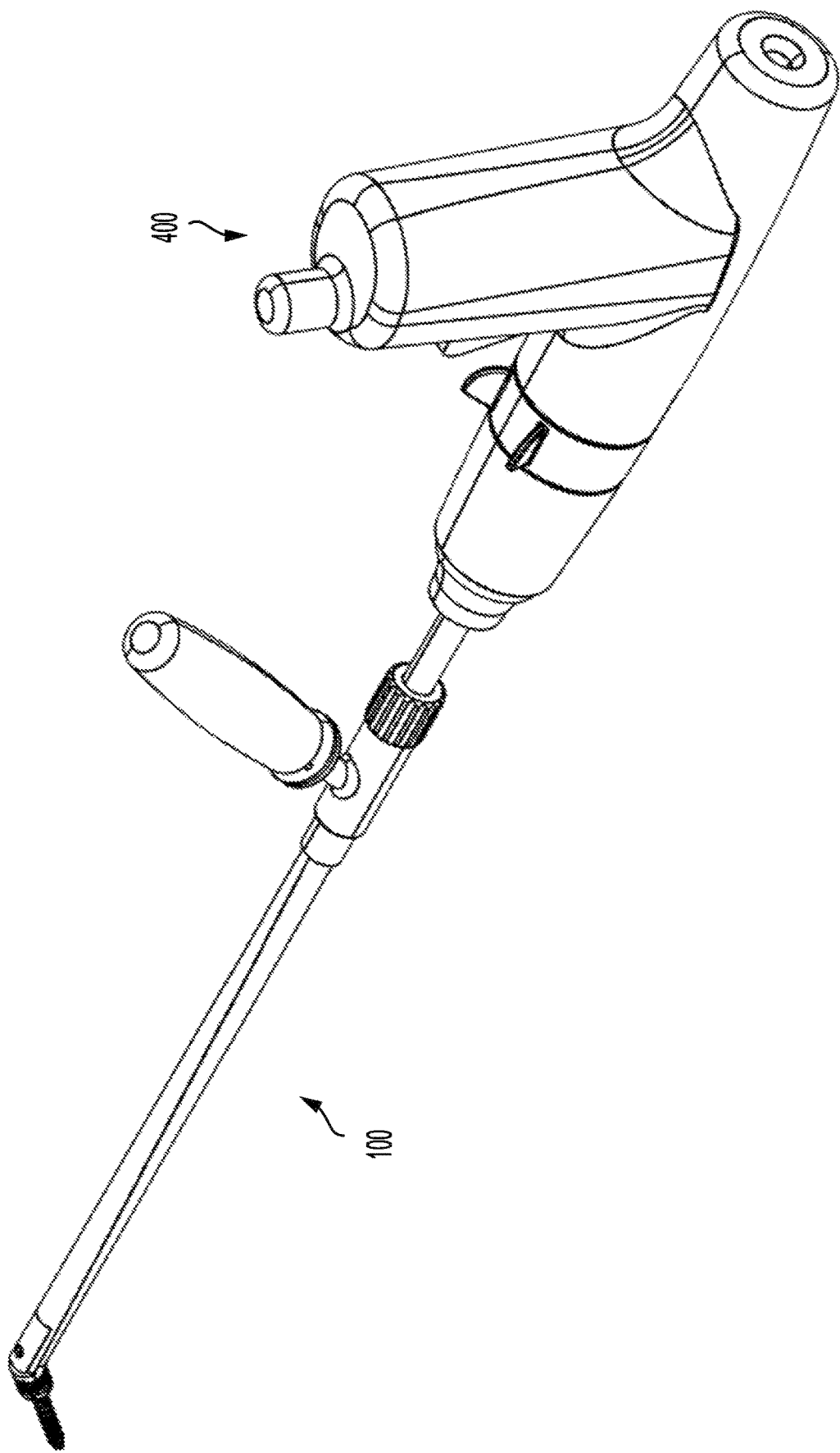
FIG. 21 is a perspective view of an example screwdriver coupled to a powered driver in accordance with the principles of the present disclosure.
Figure 22:
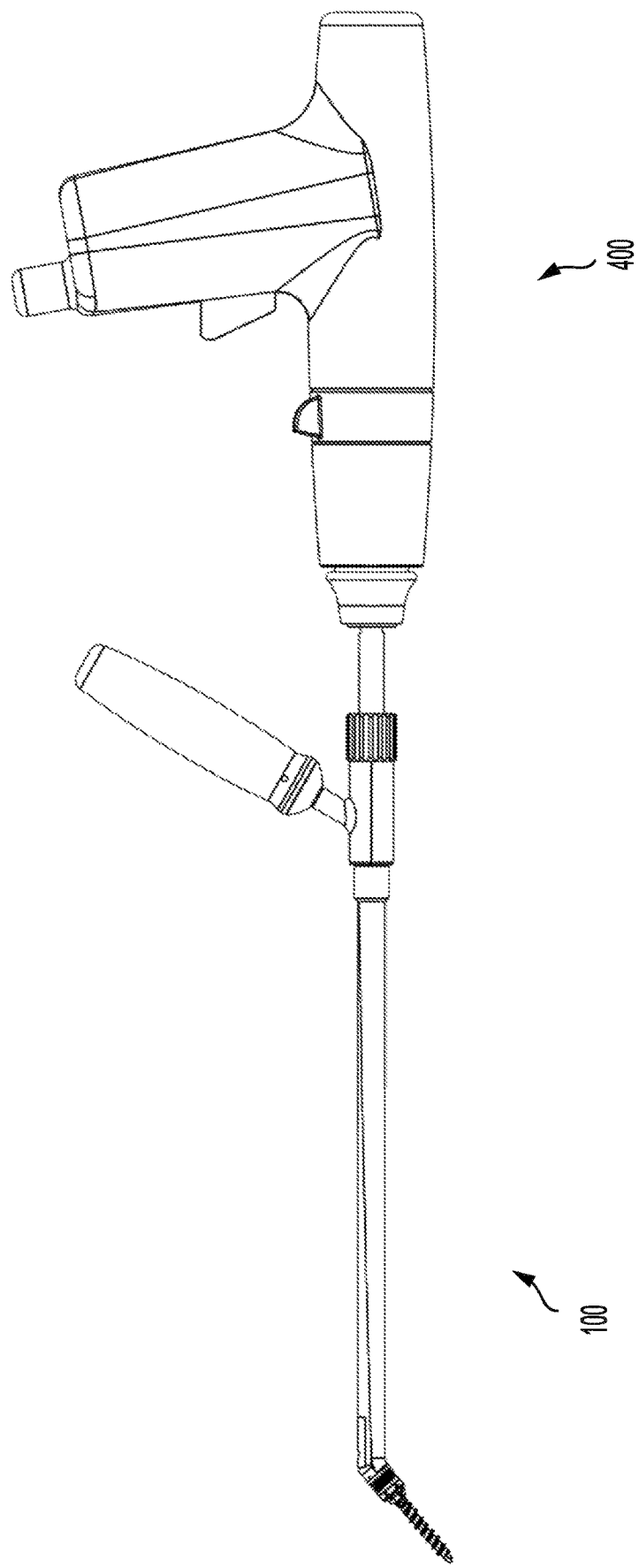
FIG. 22 is a side view of an example screwdriver coupled to a powered driver in accordance with the principles of the present disclosure.

FIGS. 19 and 20 illustrate an example screwdriver 100 operably coupled to a manual hand driver 300 in accordance with the principles of the present disclosure. Hand driver 300 may selectively couple and uncouple with drive portion 102a of drive shaft 102. Hand driver may be of a fixed type or a ratcheting type. In some embodiments, the hand driver 300 includes a ratchet adjusting mechanism including, e.g., a ratchet wheel, spring, pawl, etc. Manual hand driver 300 may be configured to adjust a driving direction of the drive shaft 102 in at least two ways. First, ratchet-adjusting mechanism may enable drive shaft 102 to apply a rotation force to a bone screw 200 when turned in a counterclockwise direction and to not apply a rotation force to the bone screw 200 when turned in a counterclockwise direction. Second, ratchet-adjusting mechanism may enable drive shaft 102 to apply a rotation force to a bone screw 200 when turned in a counterclockwise direction and to not apply a rotation force to the bone screw 200 when turned in a counterclockwise direction. In some embodiments, hand driver 300 may also be torque adjustable similar to a torque wrench. At least one example of a manual hand driver 300 may be the commercially available Medtronic QC handle. FIGS. 21 and 22 illustrate an example screwdriver 100 operably coupled to a powered driver 400 in accordance with the principles of the present disclosure. Powered driver 400 may be powered by any means, e.g., electrically operated or pneumatically operated.

Figure 23:
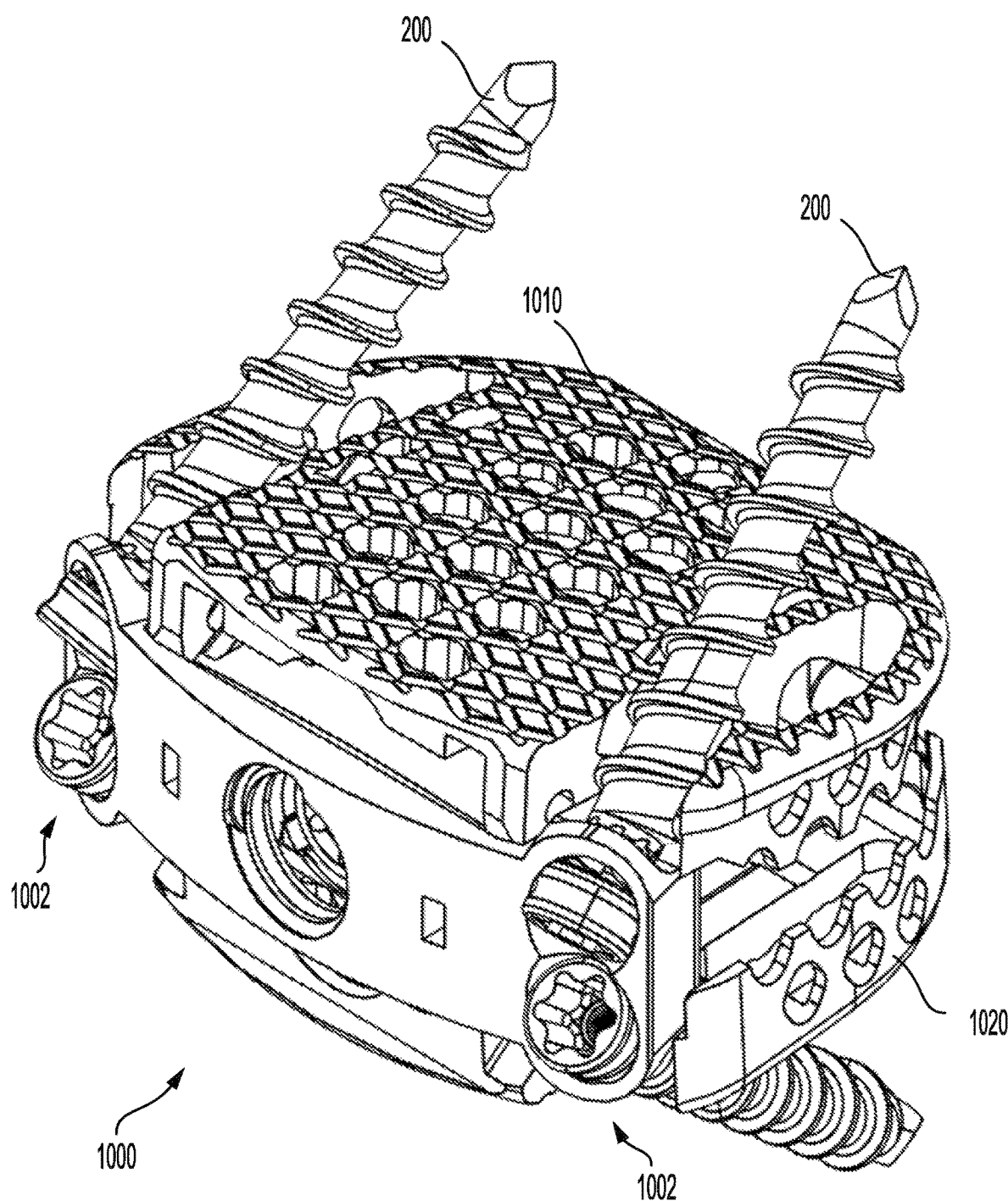

FIG. 23 is a perspective view of an example medical device 1000 that includes a plurality of inclined bone screw apertures 1002. Consistent with the principles of the disclosure, various example screwdrivers 100 may include a tip portion 106 that is angled at a degree β with respect to a longitudinal direction of housing 110. In some embodiments, tip portion 106 may be angled such that the degree β corresponds to the desired inclination of bone screw 200 and/or bone screw apertures 1002. Additionally, tip portion 106 may be angled at a degree β that accounts for both (1) the desired inclination of bone screw 200 and/or bone screw apertures 1002; and (2) the particular type of surgery (anterior, lateral, oblique, etc.) and surgical access opening available to a surgeon.

What is claimed is:

1. A screwdriver, comprising:
    a housing extending in a longitudinal direction and terminating at an angled tip portion, the angled tip portion forming an obtuse angle with respect to the longitudinal direction;
    a rotatable drive shaft, the drive shaft including a drive portion disposed at a distal end thereof, a drive end disposed at a proximal end thereof, and a main shaft portion extending in the longitudinal direction through the housing;
    an interlocking mechanism configured to interlock the main shaft portion and the drive end, the interlocking mechanism being configured to transfer a rotational force applied to the drive portion of the drive shaft through the angled tip portion to the drive end of the drive shaft;
    an elastic retaining clip supported by the drive portion and being configured to have a bone screw securely attached therein at a clipping force and progressively release the bone screw therein at an extraction force, the elastic retaining clip being removably and operably coupled with the drive end of the drive shaft;
    a first spring contacting the elastic retaining clip and the angled tip portion, the first spring being configured to facilitate the progressive release of the bone screw; and
    a second spring contacting the elastic retaining clip and the angled tip portion, the second spring being configured to facilitate the progressive release of the bone screw,
    wherein the drive end of the drive shaft extends through the angled tip portion,
    wherein the first spring and second spring each contact the elastic retaining clip and the angled tip portion,
    wherein the first spring is disposed, at least partly, within a central cavity of the second spring, and
    wherein the second spring biases the retaining clip away from the angled tip portion.

2. The screwdriver of claim 1, further comprising a positioning handle configured for an end user to securely maintain the screwdriver in place.

3. The screwdriver of claim 2, wherein the positioning handle is angled with respect to the housing and extends towards the distal end.

4. The screwdriver of claim 1, wherein the elastic retaining clip is configured to rotate with the drive portion of the drive shaft.

5. The screwdriver of claim 1, wherein the elastic retaining clip further comprises at least one bump configured to facilitate the retention of the bone screw by contacting the bone screw.

6. The screwdriver of claim 5, wherein the bone screw includes an indent extending circumferentially around a head portion of the bone screw and the at least one bump is configured to contact the bone screw and be seated, at least partially, within the indent.

7. The screwdriver of claim 1, wherein the elastic retaining clip further comprises at least one protrusion disposed at an end portion thereof configured to facilitate the retention of the bone screw.

8. The screwdriver of claim 7, wherein the at least one protrusion is radially inset with respect to a head portion of the bone screw and is configured to contact an end portion of the head portion of the bone screw to thereby facilitate the retention of the bone screw.

9. The screwdriver of claim 1, wherein the elastic retaining clip further comprises at least one tapered portion that progressively tapers along the retaining clip to an outermost end thereof.

10. The screwdriver of claim 1, wherein the tapered portion is configured to contact a circumferential surface of a head portion of the bone screw.

11. The screwdriver of claim 1, wherein the interlocking mechanism is a geared mechanism further comprising:
a first group of teeth disposed at a proximal end of the main shaft portion and extending in the longitudinal direction; and
a second group of teeth disposed at a distal end of the drive end and extending in a direction parallel with respect to the angled tip portion,
wherein the first group of teeth are meshed with the second group of teeth to thereby transfer a rotational force applied to the drive portion to the drive end.

12. The screwdriver of claim 1, wherein the interlocking mechanism is a joint mechanism further comprising:
a spherical portion seated in a housing area of the tip portion, the spherical portion being operably coupled to the main shaft portion at a proximal end thereof and fixedly coupled to the drive end at a distal end thereof,
wherein the spherical portion includes at least one aperture configured to receive a proximal end of the main shaft portion therein and a pin to operably couple the main shaft portion to the spherical portion.

13. The screwdriver of claim 1, wherein the clipping force is about 2.5 N and the extraction force is about 15 N.

14. The screwdriver of claim 1, wherein a ratio of the clipping force to the extraction force is about 1:6.

15. The screwdriver of claim 1, further comprising a manual hand driver configured to operably couple with the drive portion of the drive shaft.

16. The screwdriver of claim 1, further comprising a powered driver configured to operably couple with the drive portion of the drive shaft.

* * * * *